US006444744B1

(12) United States Patent
Fujimaru et al.

(10) Patent No.: US 6,444,744 B1
(45) Date of Patent: *Sep. 3, 2002

(54) HYDROPHILIC RESIN, ABSORBENT ARTICLE, AND ACRYLIC ACID FOR POLYMERIZATION

(75) Inventors: Hirotama Fujimaru; Kunihiko Ishizaki; Nobuyuki Harada, all of Suita; Sei Nakahara, Himeji, all of (JP)

(73) Assignee: Nippon Shokubai Co., Ltd. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/258,503

(22) Filed: Feb. 27, 1999

(30) Foreign Application Priority Data

Mar. 11, 1998 (JP) ............................................ 10-060060

(51) Int. Cl.$^7$ ........................ C08F 20/06; C08F 220/06; C08J 3/24; C08L 33/02
(52) U.S. Cl. ..................... 524/556; 526/77; 526/317.1; 526/318.5
(58) Field of Search ............................... 526/77, 317.1, 526/318.5; 524/556

(56) References Cited

U.S. PATENT DOCUMENTS

| 3,948,867 A | * | 4/1976 | Bader et al. .............. 526/317.1 |
| 4,625,059 A | | 11/1986 | Shibano et al. |
| 4,654,039 A | * | 3/1987 | Brandt et al. ................ 526/207 |
| 4,794,166 A | | 12/1988 | Engelhardt et al. |
| 4,929,717 A | | 5/1990 | Chmelir |
| 4,959,060 A | | 9/1990 | Shimomura et al. |
| 4,972,019 A | | 11/1990 | Obayashi et al. |
| 4,985,514 A | | 1/1991 | Kimura et al. |
| 5,229,488 A | | 7/1993 | Nagasuna et al. |
| 5,422,405 A | | 6/1995 | Dairoku et al. |
| 5,597,873 A | | 1/1997 | Chambers et al. |

FOREIGN PATENT DOCUMENTS

| EP | 0 574 260 A1 | 12/1993 |
| EP | 0 668 080 A2 | 8/1995 |
| EP | 0 780 424 A1 | 6/1997 |
| EP | 0 837 076 A2 | 4/1998 |
| FR | 1.571.371 | 6/1969 |
| GB | 1 226 141 | 3/1971 |
| JP | 03031306 A | 2/1991 |
| JP | 05086251 A | 4/1993 |
| JP | 06211934 A | 8/1994 |

* cited by examiner

*Primary Examiner*—Donald R. Wilson
(74) *Attorney, Agent, or Firm*—Haugen Law Firm PLLP

(57) ABSTRACT

The invention provides a hydrophilic resin and an absorbent article, both of which display still less coloring and discoloring when preserved for a long time. The hydrophilic resin is any one of: 1) a hydrophilic resin, obtained by a process including the step of polymerizing a monomer component including a major proportion of either one or both of acrylic acid and its salt which merely have a content of at most 0.20 ppm in total of hydroquinone and benzoquinone; 2) a hydrophilic resin, comprising a major proportion of an acrylic polymer and a minor proportion of either one or both of hydroquinone and benzoquinone, with the hydrophilic resin further comprising a quinhydronation inhibitor of 10~1,000,000 times the total weight of hydroquinone and benzoquinone; 3) a hydrophilic resin, comprising a major proportion of an acrylic polymer and merely having a coloring degree (YI) of at most 20 after being left under conditions of the open system, 70° C., 65% RH for 1 week; and 4) a hydrophilic resin, which is a water-absorbent resin and is surface-crosslinked or surface-impregnated with a polyhydric alcohol and displays pH of 5.5 or less in a physiological salt solution and has an absorption capacity of 20 g/g or more for a physiological salt solution under a load of 50 g/cm$^2$. In addition, the absorbent article comprises the above hydrophilic resin.

17 Claims, 1 Drawing Sheet

//HYDROPHILIC RESIN, ABSORBENT ARTICLE, AND ACRYLIC ACID FOR POLYMERIZATION

BACKGROUND OF THE INVENTION

A. Technical Field

The present invention relates to a hydrophilic resin, an absorbent article, and acrylic acid for polymerization.

B. Background Art

In recent years, water-absorbent resins, having water-absorbency to the high degree, has been developed as some of hydrophilic resins and are practically used as absorbent articles, such as disposable diapers and sanitary napkins, in combination with fibrous base materials such as cotton, pulp, paper, and sponge. As to the water-absorbent resin, acrylic polymers such as crosslinked partially neutralized polyacrylic acids are industrially most commonly used because of their high water-absorbency, which acrylic polymers are obtained using either one or both of acrylic acid and its salt as the monomer (e.g. JP-A-62-054751).

The above conventional water-absorbent resins have problems in that when preserved for a long time (4 months or longer), they color or discolor to brown or yellow even at room temperature, so the absorbent articles using such water-absorbent resins greatly lose their goods values during preservation.

Concerned with such problems, JP-A-05-086251 regards it as a factor that a very small amount of transition metal in the water-absorbent resin generates radical species to cause unpreferable reactions such as decomposition of the water-absorbent resin and the cleavage of polymer chains, and thus the above document proposed an art in which the coloring with time is prevented by scavenging the transition metal using organic phosphoric acid compounds or their salts.

However, the above prior improving art as disclosed in JP-A-05-086251 has problems as follows.

According to the above prior improving art, as to the water-absorbent resin powder standing alone, its coloring degree (YI) is around 7.8 in the initial stage, but increases up to 35.0~37.2 when the resin powder is left at 70° C. under 65% RH in the closed system for 1 week (Comparative Examples 1~3 of the '251 publication), whereas when the organic phosphoric acid compound is added in a ratio of 0.1~0.63 weight % to the resin powder, the coloring degree (YI) is 20.2~20.8 after 1 week, so it is assumed in the '251 publication that the change of the coloring degree ($\Delta$YI) could be suppressed to 12.4~13.0 (Examples 1~3 of the '251 publication). Indeed the above prior improving art may suppress the coloring with time to some extent, but the addition of the organic phosphoric acid compound not only does complicate the process, but also is not necessarily favorable in view, for example, of the safety. In addition, even Example 2 that provides the most excellent results among the examples of preferred embodiments, as set forth in the above prior improving art, merely results in YI=12.2 and $\Delta$YI=about 4.4 when the resin is left at 70° C. under 65% RH for 1 week, and, naturally, problems of great coloring or discoloring occur when the resin is preserved for a still longer time.

Water-absorbent resins or their products (absorbent articles such as diapers) are internationally traded and, in many cases, preserved for a long time or under high humidity. Therefore, the problems of the coloring often occur. problems and sufficiently bears being practically used. On the basis of such observation results, the present inventors devised the below-mentioned new coloring evaluation method.

Incidentally, some conventional resins, as obtained by reversed-phase suspension polymerization, display the coloring degree (YI) of a little more than 20, but a large amount of hydrophobic organic solvent is used for the reversed-phase suspension polymerization, so the resultant resin has problems on the safety due to the residue of the organic solvent and is therefore not fit for sanitary materials, and further has problems on the cost for the use of the organic solvent. In addition, there are further problems in that the resultant water-absorbent resin comprises spherical fine particles and is therefore difficult to mix with or bind to pulp. and further. is generally insufficient with regard to the crosslinking degree of the surface neighborhood. As a result, the absorption capacity under a load or the liquid permeability is low.

In the above prior improving art, the coloring evaluation is carried out to water-absorbent resins as obtained by polymerization, drying, and pulverization, but there are also problems in that no sufficient study is made about influences to the coloring of factors, such as surface neighborhood crosslinking (as carried out after polymerization and drying) of water-absorbent resin particles, or particle size, shape, or water content of the water-absorbent resin. Generally, examples of the properties which water-absorbent resins should have are as follows: upon contact with aqueous liquids such as body fluids, excellent water absorption amount or speed, the liquid permeability, the gel strength of the swollen gel, the smallness of water-soluble content or monomer residue, the suction power to suck up water from a base material In recent years, the amount of water-absorbent resin, as used for absorbent articles, tends to increase. The above prior improving art can prevent the coloring if the amount of water-absorbent resin as used is small, but the above prior improving art cannot respond to a large amount of water-absorbent resin. Thus, it is desired to improve the water-absorbent resin itself, namely, to develop a water-absorbent resin that displays extremely little coloring.

The above prior improving art has further problems on the coloring evaluation for the following reason. That is to say, the coloring evaluation in the prior improving art is carried out in the closed system. However, sanitary materials including water-absorbent resins are usually preserved not in an entirely sealed state, but in the at least partially open system (for example, sanitary materials have sewing machine stitches to open their packages), so the coloring evaluation needs to be carried out in the open system.

In the process of diligent study to achieve the below-mentioned objects, the present inventors tried to evaluate the coloring in the open system with regard to water-absorbent resins now on the market. As a result, the coloring degree (YI) was 40~50 or more. That is to say, the conventional water-absorbent resins displayed the great coloring degree in the open system. Thus, the present inventors confirmed that the coloring evaluation in the closed system according to the above prior improving art had a tendency to display a lower value than that in the open system (for example, coloring degree (YI)=12.2 in Example 2 of the above prior improving art increases to about 23~about 30 in the open system evaluation), and further that if YI=20 or less in the open system coloring evaluation, such a water-absorbent resin can solve the above containing aqueous liquids. Among these properties, the absorption actions under a load (e.g. absorption capacity under a load or liquid permeability under a load) are made much of as the fundamental properties which water-absorbent resins should have. There are known methods in which the surface of water-absorbent resins is crosslinked with surface-crosslinking agents for the purpose of obtaining water-absorbent resins of high absorption capacity under a load (EP 668080, U.S. Pat. No. 5,597,873, U.S. Pat. No. 5,422,405, U.S. Pat. No. 5,409,771). In production processes for water-absorbent resins, not only the above surface-crosslinking step but also the drying step of the water-absorbent resin involves heating of the water-absorbent resin. In the above surface-crosslinking step, the polyhydric alcohol is preferable in view of the safety or the resulting properties and is therefore often used, but the polyhydric alcohol makes crosslinking by dehydration and is therefore low reactive. Thus, the surface-crosslinking that involves the use of the polyhydric alcohol needs relatively high temperature or a long time. If the above property improvement or productivity is made much of, the surface-crosslinking or drying step needs heating for a long time and further at high temperature. As a result, thermal degradation or coloring of the water-absorbent resin is unavoidable. Thus, the improvement is needed. Particularly, the water-absorbent resin as surface-crosslinked with surface-crosslinking agents such as polyhydric alcohols has a high tendency to easily become colored during the production or with time thereafter, the above improvement is strongly demanded.

When various absorbent articles such as disposable diapers are produced, it is necessary to combine with a fibrous base material a large quantity of water-absorbent resin which has very high hygroscopicity and of which the main current is powder. Recently, there are increasing problems in that, depending on the environment of working or on weather conditions, powders of the water-absorbent resin cause blocking on the way of the popper or line or adhere to apparatuses, so the absorbent article cannot stably be produced. However, conventional water-absorbent resins as improved upon the above blocking property undergo the deterioration of the absorption capacity under a load and some of the other absorption properties due to the addition of a blocking improvement agent, and further, as to absorbent articles with high resin concentration, the desorption (wet back) of absorbed body fluid tends to increase due to the addition of the above improvement agent. Thus, it is demanded not to add the above improvement agent.

SUMMARY OF THE INVENTION

A. Objects of the Invention

A first object of the present invention is to provide a new hydrophilic resin, such as water-absorbent resin, and a new absorbent article, both of which display still less coloring and discoloring when preserved in the open system for a long time.

A second object of the present invention is to provide a new hydrophilic resin, such as water-absorbent resin, and a new absorbent article, both of which display little deterioration, coloring, or discoloring due to heating at high temperature for a long time in the surface-crosslinking or drying step.

A third object of the present invention is to improve the hygroscopic fluidity (blocking resistance of the water-absorbent resin under high humidity conditions).

B. Disclosure of the Invention

In the process of diligent study to achieve the above objects, the present inventors further inferred that the transition metal, which is regarded in JP-A-05-086251 as a factor of the coloring, is not the only one factor of the coloring. Thus, the inventors studied about other factors with encouragement to themselves and with great efforts. The starting materials, as used to produce the water-absorbent resin, usually comprise ten and several kinds of materials, such as bases for neutralization (e.g. sodium hydroxide), crosslinking agents, polymerization initiators, organic solvents, and water, in addition to one or more monomers such as acrylic acid. Among theses materials, acrylic acid is industrially produced commonly by a propylene gas phase oxidation process. Acrylic acid resultant from such a process contains by-products or impurities such as acetic acid, formaldehyde, acrolein, propionic acid, maleic acid, acetone, furfural, and benzaldehyde. Thus, purification is carried out by methods such as solvent extraction and azeotropic dehydration for the purpose of removing those by-products or impurities. However, because acrylic acid easily polymerizes, it is necessary that the purification is carried out in the presence of polymerization inhibitors. Effective polymerization inhibitors are, for example, hydroquinone, hydroquinone monomethyl ether, copper salts, and methylene blue, and particularly, it is common to mainly use hydroquinone, which is the cheapest of the above polymerization inhibitors, and to supplementarily use other expensive polymerization inhibitors (e.g. hydroquinone monomethyl ether). For example, JP-A-10-017524 proposes to use a mixture of an aqueous acetic acid solution and a copper compound as a polymerization inhibitor in the above purification step, but in all the examples of preferred embodiments as set forth in this prior art document, hydroquinone is jointly used with the above mixture.

Because hydroquinone has a high boiling point (boiling point: 285° C./730 Torr, melting point: 174° C.), it is conventionally thought that even if hydroquinone is used during distillation, hydroquinone does not mingle into vapor of acrylic acid (boiling point: 141° C./755 Torr), and therefore is not contained in the finally purified acrylic acid. In fact, on packages of commercially available acrylic acid, it is clearly written that hydroquinone monomethyl ether is contained as the polymerization inhibitor by about 200 ppm, but on none of them, it is clearly written that hydroquinone is contained. Thus, it is conventionally thought that acrylic acid is free from hydroquinone. However, the present inventors found that hydroquinone is contained in purified acrylic acid, although its content is extremely small. One of factors thereof is considered as follows. As is shown by formula (1) below,

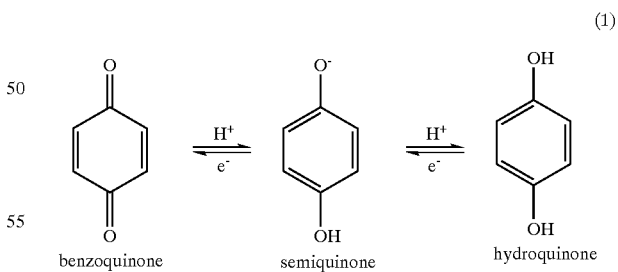

(1)

hydroquinone has an equilibrium relation with benzoquinone, and benzoquinone has subliming-property, so hydroquinone becomes benzoquinone because of being heated during distillation on the way of purification to mingle into acrylic acid, and then reverts to benzoquinone. In addition, part of hydroquinone, which mingled into purified acrylic acid, bimolecularly associates in a state of semiquinone (isolation of semiquinone itself is assumed to be impossible) that is an intermediate state in equilibrium between hydroquinone and benzoquinone, thus forming an associated matter (quinhydrone) of formula (2) below (either (A) or (B)):

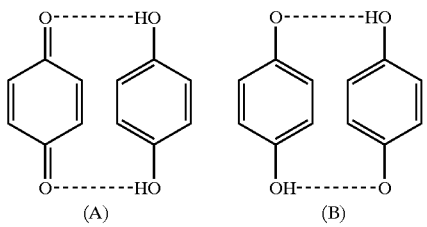

(2)

(A)    (B)

The present inventors completed the present invention by finding that this associated matter (quinhydrone) causes the coloring with time. The above-mentioned ten and several kinds of starting materials (e.g. monomers, crosslinking agents, solvents, polymerization initiators) contain various impurities, and the monomer acrylic acid also contains various impurities, and also as to the polymerization inhibitor, many kinds are known. However, the present inventors found that: among the above polymerization inhibitors, surprisingly, an extremely small amount of hydroquinone in acrylic acid causes the coloring with time of the water-absorbent resin; for example, though hydroquinone monomethyl ether is also included in the hydroquinone type polymerization inhibitors similarly to hydroquinone, hydroquinone monomethyl ether has no problem of the coloring with time of the water-absorbent resin, and other impurities (e.g. acrolein, benzaldehyde, acetic add, propionic acid), either, have no problem of the coloring with time of the water-absorbent resin.

Because unneutralized polyacrylic acid is acidic (pH= about 3.0), the ratio for the equilibrium to move in a direction from hydroquinone to benzoquinone is low, and if the hydroquinone content is extremely small, the probability to form the associated matter of formula (2) is low. However, the present inventors found a fact that it is a great cause of the coloring of the water-absorbent resin that, because the water-absorbent resin is required to be neutral (pH=about 6~about 8 (as to commercially available ones, pH=about 6.1)) from its usage, the ratio for the equilibrium to move in a direction from hydroquinone to benzoquinone is high, and the probability to form the associated matter of formula (2) is also high. That is to say, it was found that, because the water-absorbent resin is a crosslinked product of a neutral polyacrylic acid, it becomes colored more greatly than water-soluble polyacrylic acids, for example, entirely neutralized polyacrylic acids (neutralization ratio=100 mol %) or unneutralized polyacrylic acids.

For the above reason, the present inventors thought that employing either one or both of the following methods ① and ② is effective for preventing the coloring with time of the water-absorbent resin.

① A method involving reduction of the ratio for the equilibrium to move in a direction from hydroquinone to benzoquinone to form the associated matter (quinhydrone) of formula (2) in the water-absorbent resin. For achieving this, it is effective to add an quinhydronation inhibitor to the water-absorbent resin.

② A method in which a water-absorbent resin is produced using acrylic acid with a smaller hydroquinone content than conventional cases, thereby rendering the hydroquinone content in the resultant water-absorbent resin small (actually, as is mentioned above, hydroquinone has the equilibrium relationship with benzoquinone, so the hydroquinone content is the total of hydroquinone and benzoquinone). For achieving this, it is effective to produce a water-absorbent resin by polymerizing a monomer component including a major proportion of either one or both of acrylic acid and its salt which merely have a content of at most 0.20 ppm in total of hydroquinone and benzoquinone.

Then, the present inventors thought that these findings are applicable to the coloring prevention of not only the water-absorbent resin, but also all hydrophilic resins that are produced from acrylic acid.

That is to say, the present invention provides the following constitutions:

(1) A hydrophilic resin, obtained by a process including the step of polymerizing a monomer component including a major proportion of either one or both of acrylic acid and its salt which merely have a content of at most 0.20 ppm in total of hydroquinone and benzoquinone.

(2) A hydrophilic resin according to constitution (1) above, wherein the polymerization is aqueous solution polymerization.

(3) A hydrophilic resin according to constitution (1) or (2) above, obtained by a process further including the step of heat-drying at 100~300° C. within 3 hours after the polymerization.

(4) A hydrophilic resin according to any one of constitutions (1)~(3) above, comprising particles of the irregular pulverized shape, of which 50 weight % or more have a particle diameter of 300 µm or more.

(5) A hydrophilic resin according to any one of constitutions (1)~(4) above, which merely has a water content of at most 2 weight %.

(6) A hydrophilic resin according to any one of constitutions (1)~(5) above, which is a partially neutralized resin.

(7) A hydrophilic resin, comprising a major proportion of an acrylic polymer and a minor proportion of either one or both of hydroquinone and benzoquinone, with the hydrophilic resin further comprising a quinhydronation inhibitor of 10~1,000,000 times the total weight of hydroquinone and benzoquinone.

(8) A hydrophilic resin according to constitution (7) above, wherein the quinhydronation inhibitor is methylenebisacrylamide.

(9) A hydrophilic resin, comprising a major proportion of an acrylic polymer and merely having a coloring degree (YI) of at most 20 after being left under conditions of the open system, 70° C., 65% RH for 1 week.

(10) A hydrophilic resin according to constitution (9) above, which merely displays a change of the coloring degree (YI) by at most 4.

(11) A hydrophilic resin according to constitution (9) or (10) above, wherein the acrylic polymer is a polymer as obtained by a process including the step of aqueous solution polymerization.

(12) A hydrophilic resin according to any one of constitutions (9)~(11) above, comprising particles of the irregular pulverized shape, of which 50 weight % or more have a particle diameter of 300 µm or more.

(13) A hydrophilic resin according to any one of constitutions (1)~(12) above, which is a water-absorbent resin.

(14) A hydrophilic resin according to constitution (13) above, which displays pH of 5.5 or less in a physiological salt solution.

(15) A hydrophilic resin according to constitution (13) or (14) above, of which 50 weight % or more have a particle diameter of 300 µm or more.

(16) A hydrophilic resin according to any one of constitutions (13)~(15) above, of which the surface neighborhood of the particles are crosslinked.

(17) A hydrophilic resin according to constitution (16) above, wherein the crosslinking temperature during the surface-crosslinking is in the range of 100~250° C., and the crosslinking time is within 3 hours.

(18) A hydrophilic resin according to constitution (16) or (17) above, wherein the surface-crosslinking is carried out by a dehydration reaction.

(19) A hydrophilic resin according to constitution (18) above, wherein the crosslinking agent for the dehydration reaction is a polyhydric alcohol.

(20) A hydrophilic resin according to any one of constitutions (13)~(19) above, which has an absorption capacity of 20 g/g or more for a physiological salt solution under a load of 50 g/cm$^2$.

(21) A hydrophilic resin, which is a water-absorbent resin and is surface-crosslinked or surface-impregnated with a polyhydric alcohol and displays pH of 5.5 or less in a physiological salt solution and has an absorption capacity of 20 g/g or more for a physiological salt solution under a load of 50 g/cm$^2$.

(22) An absorbent article, comprising:
    an absorbent layer including the hydrophilic resin as recited in any one of constitutions (13)~(21) above and a fibrous base material;
    a liquid-permeable surface sheet; and
    a liquid-impermeable back sheet;
    wherein the weight ratio, α, of the hydrophilic resin to the total of the hydrophilic resin and the fibrous base material is 0.3 or more.

(23) Acrylic acid for polymerization, which is acrylic acid as obtained using hydroquinone in its production process and merely has a content of at most 0.20 ppm in total of hydroquinone and benzoquinone.

(24) Acrylic acid for polymerization according to constitution (23) above, which is used for polymerization to give a hydrophilic resin.

(25) Acrylic acid for polymerization according to constitution (24) above, wherein the hydrophilic resin is a water-absorbent resin.

(26) A use of the hydrophilic resin as recited in any one of constitutions (1)~(21) above under a relative humidity of 50% or higher.

(27) A coloring evaluation method of a hydrophilic resin, comprising the step of judging the coloring degree that the hydrophilic resin displays when left under conditions of the open system, a certain temperature, and a certain humidity.

These and other objects and the advantages of the present invention will be more fully apparent from the following detailed disclosure.

DETAILED DESCRIPTION OF THE INVENTION

Figure 1:
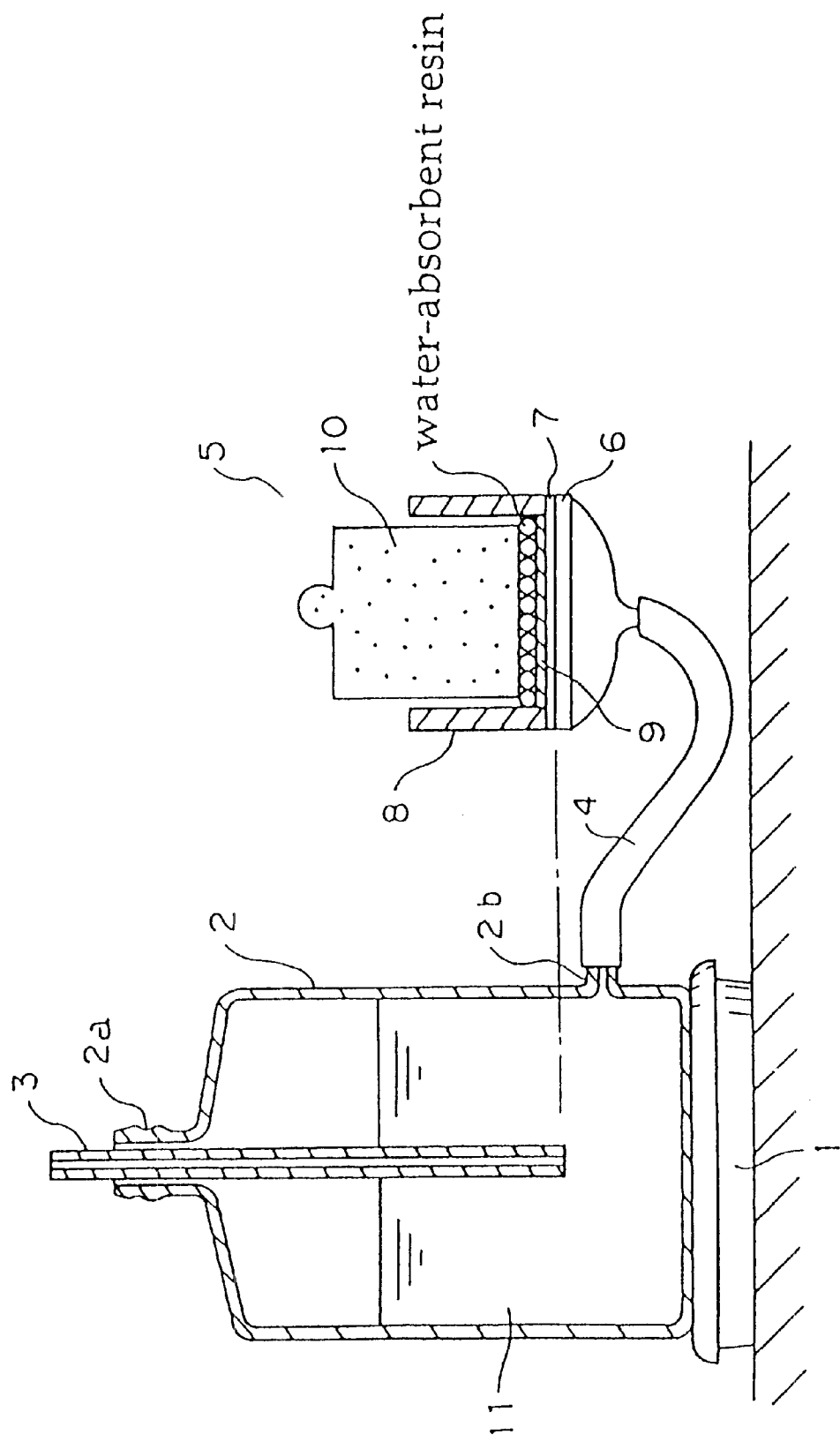
FIG. 1 illustrates a measurement apparatus for the water absorption capacity under a load as used in the present invention.

The quinhydronation inhibitor, which is used in method ① above and used as one component of the present invention hydrophilic resin, is explained below. The ratio to form the associated matter of formula (2) can be made low by adding the quinhydronation inhibitor to a hydrophilic resin which comprises a major proportion of an acrylic polymer and a minor proportion of either one or both of hydroquinone and benzoquinone. The quinhydronation inhibitor is a substance having a property to inhibit semiquinone, as formed by equilibrium from either one or both of hydroquinone and benzoquinone, from associating bimolecularly to form quinhydrone. The quinhydronation inhibitor is not especially limited if it serves to inhibit quinhydrone from forming from either one or both of hydroquinone and benzoquinone. Specific examples thereof include compounds having 2 or more —(NH—CO)-bonds per molecule. The reason why the compounds having 2 or more —(NH—CO)-bonds per molecule are effective to inhibition of quinhydronation is indefinite, but seems to be that hydroquinone is stabilized by some action. Among the compounds having 2 or more —(NH—CO)-bonds per molecule, those which have a molecular weight of 1,000 or less are preferable, because it is inferred that when the molecular weight is high, the compound hardly penetrates or moves into the hydrophilic resin, so the quinhydronation inhibition effect is hardly exhibited.

Examples of the compounds having 2 or more —(NH—CO)-bonds per molecule include compounds having —(NH—CO)—R—(CO—NH)-bonding or (CO—NH)—R—(NH—CO)-bonding in molecule (wherein: R denotes a single bond or an organic group). Specific examples thereof include methylenebisacrylamide of formula (3) below:

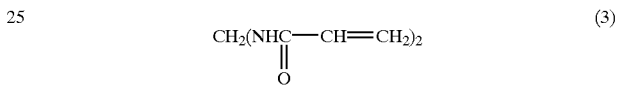

(3)

and 2,2'-oxyamidobis-[ethyl-3-(3,5-di-tert-butyl-4-hydroxyphenyl) propionate of formula (4) below:

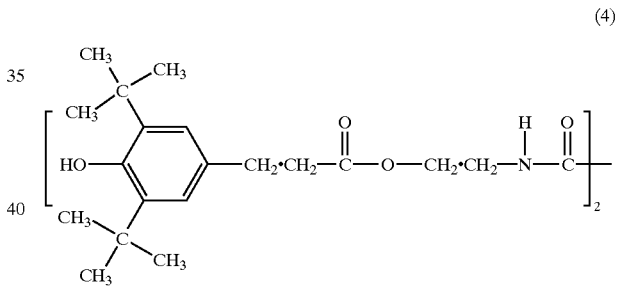

(4)

Particularly, methylenebisacrylamide is preferable in view of the effects.

The amount of the quinhydronation inhibitor, as added, needs to be the weight ratio of 10~1,000,000 times, preferably 50~500,000 times, particularly preferably 100~500,000 times, of the total of hydroquinone and benzoquinone in the hydrophilic resin. In the case where the weight ratio is smaller than 10 times, the quinhydronation inhibition effect is little. On the other hand, in the case where the weight ratio exceeds 1,000,000 times, the ratio of the hydrophilic resin substantially falls, so the water absorption properties might deteriorate when the hydrophilic resin is, for example, a water-absorbent resin. The reason why the above ratio is based on the total of hydroquinone and benzoquinone is that as is mentioned above, there are the equilibrium relations between hydroquinone and benzoquinone.

Incidentally, it is known that when the monomer component is polymerized N,N'-methylenebisacrylamide is used as the internal-crosslinking agent of the water-absorbent resin, and it is considered that part of N,N'-methylenebisacrylamide might not be bound into the structure of the water-absorbent resin, but be present in the free form in the water-absorbent resin. However, when N,N'- methylenebisacrylamide is used as the internal-crosslinking agent, the amount of N,N'-methylenebisacrylamide, remaining in the water-absorbent resin as obtained by polymerizing a hydrophilic unsaturated monomer, is usually not more than the detection limit, so N,N'-methylenebisacrylamide cannot inhibit hydroquinone in the water-absorbent resin from becoming quinhydrone.

An explanation is made on acrylic acid and its salt, which are used in method ② above and used as a starting material of the hydrophilic resin of the present invention and merely have a content of at most 0.20 ppm in total of hydroquinone and benzoquinone.

Examples of publicly known industrial production processes for acrylic acid include: propylene gas phase oxidation process, ethylene cyanohydrin process, high pressure Reppe process, improved Reppe process, ketene process, and acrylonitrile hydrolysis process. Among them, the propylene gas phase oxidation process is most commonly employed.

The propylene gas phase oxidation process is a process in which acrylic acid is obtained from propylene via acrolein by a catalytic gas phase oxidation process. The reaction is usually carried out by two steps using water vapor as a diluent. There are advantages in that the conversion of propylene is almost 100%, so the yield is high. In the propylene gas phase oxidation process, an aqueous acrylic acid solution including impurities is usually obtained by causing water to absorb the reaction gas. "Crude acrylic acid" is produced by purifying and removing by-products or impurities such as acetic acid, formaldehyde, acrolein, propionic acid, maleic acid, acetone, furfural, and benzaldehyde. Then, in the case where acrylic acid is used as a starting material of the hydrophilic or water-absorbent absorbent resin, the "crude acrylic acid" is further purified to remove a very small amount of polymerization-inhibitory aldehyde, thus obtaining "purified acrylic acid." Examples of purification methods in the process of obtaining "purified acrylic acid" from "crude acrylic acid" include a distillation method and a crystallization method. Incidentally, the "purified acrylic acid" as referred to in JP-A-10-017524 is the "crude acrylic acid" in the present invention. In addition, the "acrylic acid for polymerization" as referred to in the present invention is acrylic acid as used when the resultant acrylic acid is polymerized in the form of acrylic acid as it stands or in the form of its salt neutralized. In the step of obtaining the crude acrylic acid from an aqueous acrylic acid solution and in the step of obtaining the purified acrylic acid from the crude acrylic acid, a polymerization inhibitor needs to be added, and as is mentioned above, hydroquinone that is the cheapest is mainly used in usual, and it was thought that hydroquinone as used in the above intermediate step was entirely removed because of its high boiling point. However, the present inventor found that in conventional processes, hydroquinone mingles into the finally purified acrylic acid by an extremely small amount of about 0.5~about 1 ppm, and that this extremely small amount of hydroquinone causes the coloring of the acrylic polymer.

The achievement of the aimed level, "the total content of hydroquinone and benzoquinone is at most 0.20 ppm," for example, needs carrying out the following methods: (1) a method involving reduction of the amount of hydroquinone as added as the polymerization inhibitor in the steps of obtaining purified acrylic acid from an aqueous acrylic acid solution via crude acrylic acid; and (2) a method in which the step of obtaining purified acrylic acid from crude acrylic acid is carried out more carefully than conventional cases.

The extreme example of method (1) above involves using no hydroquinone as the polymerization inhibitor and, in place thereof, using other polymerization inhibitors only. However, because hydroquinone has the advantage of being the cheapest polymerization inhibitor, hydroquinone may be used in such a small amount that it can be removed to decrease to 0.20 ppm or below in the purification step. Hydroquinone can be removed such that its content will decrease to 0.20 ppm or below even by conventional purification steps if the conventional purification steps are more carefully carried out than usual and if the total of hydroquinone and benzoquinone (deriving from the hydroquinone) in crude acrylic acid (as supplied in the step of obtaining purified acrylic acid from crude acrylic acid) with the amount of hydroquinone (as added in such a step) is generally 1,000 ppm or below, preferably 800 ppm or below, more preferably 500 ppm or below, though this depends on the total of hydroquinone and benzoquinone in crude acrylic acid. The above intermediate step, for example, involves addition of hydroquinone by 10~500 ppm. Preferable examples of other polymerization inhibitors, as fitly used instead of lessening hydroquinone, include those which give bad influence little in the hydrophilic resin, and specifically, hydroquinone monomethyl ether can be exemplified as such.

The phrase "the step . . . is carried out more carefully than conventional cases" in method (2) above means that the rectification degree is raised, for example, by increasing the number of columns or the reflux ratio (both in the case where the distillation method is employed as the purification method) or the number of times of the crystallization (in the case where the crystallization method is employed as the purification method). In addition, in the case where commercially available acrylic acid is bought, the total content of hydroquinone and benzoquinone can be reduced to 0.20 ppm or below by further purifying such acrylic acid for the same reason as above. More preferably, methods (1) and (2) above are jointly used.

That is to say, method ② above is characterized in that acrylic acid having a content of at most 0.20 ppm in total of hydroquinone and benzoquinone is intentionally produced, or selected from commercially available acrylic acid, or obtained by re-purifying commercially available acrylic acid, and that the resultant acrylic acid is used to obtain the hydrophilic resin.

The polymerization of the monomer component, including a major proportion of either one or both of acrylic acid and its salt which are obtained in the above way and merely have a content of at most 0.20 ppm, preferably at most 0.15 ppm, more preferably at most 0.10 ppm, in total of hydroquinone and benzoquinone, can give the present invention hydrophilic resin (particularly, water-absorbent resin) which has little content in total of hydroquinone and benzoquinone and displays little coloring or discoloring when preserved for a long time. However, the present invention is not limited thereto: for example, the "acrylic acid which merely has a content of at most 0.20 ppm" can be used as acrylic acid for polymerization that is a starting material of every acrylic polymer. Acrylic acid or its salt may be used as the monomer as it is, or its ester may be copolymerized as one component of monomers.

Representative examples of the acrylic polymer include hydrophilic resins. The hydrophilic resin is generally a polymer having hydrophilic functional groups, such as carboxyl, hydroxyl, amide, amino, and sulfonic acid, on polymer chains. In the present invention, examples of the hydrophilic resin include: polyacrylic acids or neutralized polyacrylic acids (in which part (about 25~about 95 mol %) or all of carboxyl groups of the polyacrylic acids are salts)

as obtained by polymerizing acrylic acid or its salt; and further, copolymers as obtained by copolymerizing acrylic acid or its salt with water-soluble or hydrophobic unsaturated monomers such as methacrylic acid, maleic acid, maleic anhydride, fumaric acid, crotonic acid, itaconic acid, vinylsulfonic acid, 2-(meth)acrylamido-2-methylpropanesulfonic acid, (meth)acryloxyalkanesulfonic acid, and their alkaline metal salts and ammonium salts, and further, N-vinyl-2 pyrrolidone, N-vinylacetoamide, (meth)acrylamide, N-isopropyl(meth)acrylamide, N-N-dimethyl (meth)acrylamide, 2-hydroxyethyl (meth)acrylate, methoxypolyethylene (meth)acrylate, polyethylene glycol (meth) acrylate, isobutylene, and lauryl (meth)acrylate.

In the present invention, when monomers other than acrylic acid are used, their amount is preferably 30 mol % or less, more preferably 10 mol % or less, of the total of acrylic acid and its salt. Incidentally, typical examples of the above hydrophilic resin include the below-mentioned water-absorbent resin or water-soluble resin.

The monomer component includes a major proportion of either one or both of acrylic acid and its salt. Particularly, the water-absorbent resin of which the coloring is a matter of grave concern, especially, partially neutralized acrylic acid polymer, is optimally applied to the present invention. As to the partially neutralized acrylic acid polymer, it is preferable that 50~95 mol %, more preferably 60~90 mol %, of the acrylic acid moiety is neutralized in view of the properties.

Examples of the salt include alkaline metal salts, ammonium salts, and amine salts, but metal salts, particularly, alkaline metal salts such as lithium salts, sodium salts, and potassium salts, are preferable. Among the alkaline metal salts, sodium salts and lithium salts are preferable. Thus, in the present invention, the lithium salts, which display high absorption capacity under a load, but somewhat easily become colored, can also favorable be used.

The neutralization may be carried out for monomers before polymerization, or during or after polymerization. For the purpose of lessening the total content of hydroquinone and benzoquinone in the finally resultant acrylic polymer, it is preferable that the usable co-monomer other than acrylic acid and its salt also merely has a content of at most 0.20 ppm in total of hydroquinone and benzoquinone. In addition, the total content of hydroquinone and benzoquinone in the entire monomers being polymerized is also preferably at most 0.20 ppm, more preferably at most 0.15 ppm, particularly preferably at most 0.10 ppm.

In the present invention, if an acid substance is allowed to remain in the hydrophilic resin (as obtained by polymerizing a monomer component including a major proportion of either one or both of acrylic acid and its salt which have little content of hydroquinone and benzoquinone in total), then it is possible to greatly move the equilibrium between hydroquinone and benzoquinone to the hydroquinone side, thereby lowering the presence ratio of semiquinone to inhibit the quinhydronation of semiquinone. Examples of the above acid substance include: hydrochloric acid, sulfuric acid, sulfurous acid, nitric acid, nitrous acid, phosphoric acid, sulfamic acid, formic acid, carbonic acid, oxalic acid, citric acid, succinic acid, benzoic acid, salicylic acid, tartaric acid, and acetic acid.

Incidentally, as is separately mentioned below, if pH of the hydrophilic resin (in a physiological salt solution) is reduced to 5.5 or below, then the coloring can further be lowered. For example, in the present invention, contrary to the conventional common sense, a crosslinked polyacrylic acid, of which 0~58 mol %, furthermore, 0~50 mol %, still furthermore, 0~40 mol %, particularly, 0~10 mol %, is neutralized, is also favorably usable as hygro-blocking-resistant and low-coloring water-absorbent resin.

In addition, though the details of the mechanism are unclear, it is inferred that if an alkaline substance is allowed to remain in the hydrophilic resin (as obtained by polymerizing a monomer component including a major proportion of either one or both of acrylic acid and its salt which have little content of hydroquinone and benzoquinone in total), then the presence ratio of semiquinone deriving from hydroquinone decreases, so that the quinhydronation of semiquinone can be inhibited. Examples of the above alkaline substance include: sodium hydroxide, potassium hydroxide, lithium hydroxide, sodium hydrogencarbonate, sodium carbonate, and ammonia.

In the present invention, if the aforementioned quinhydronation inhibitor is added to the hydrophilic resin (as obtained by polymerizing a monomer component including a major proportion of either one or both of acrylic acid and its salt which have little content of hydroquinone and benzoquinone in total), then the coloring and discoloring in long-term preservation can further be lessened.

The hydrophilic resin of the present invention has little possibility of the coloring or discoloring even in long-term preservation, specifically, merely has a coloring degree (YI) of at most 20, preferably at most 15, more preferably at most 10, most preferably at most 6, after being left under conditions of the open system, 70° C., 65% RH for 1 week. The change of the coloring degree (YI), as seen when the hydrophilic resin of the present invention is left under such conditions for 1 week, is preferably at most 10, more preferably at most 7, most preferably at most 4.

When the hydrophilic resin is produced in the present invention, bulk polymerization or precipitation polymerization can be carried out. However, considering the performance or the easiness of the polymerization control, it is preferable to carry out aqueous solution polymerization or reversed-phase suspension polymerization using the above monomer component in the form of its aqueous solution. Incidentally, the reversed-phase suspension polymerization is a polymerization method in which liquid drops of an aqueous solution of the monomer component is dispersed into an inert hydrophobic solvent, and the aqueous solution polymerization is a polymerization method in which the aqueous solution of the monomer component is directly polymerized without being dispersed into the inert solvent. Furthermore, these polymerization methods are carried out preferably under an atmosphere of an inert gas such as nitrogen or argon. In addition, the monomer component is used for polymerization after oxygen as dissolved therein has sufficiently been displaced with the inert gas. The present invention is particularly favorable for the aqueous solution polymerization which is of high productivity and gives high properties, but easily undergoes problems of coloring.

When the monomer component is used in the form of its aqueous solution in the reversed-phase suspension polymerization or aqueous solution polymerization, the concentration of the monomer component in this aqueous solution (hereinafter referred to as "aqueous monomer solution") is not especially limited, but is in the range of preferably 10~70 weight %, more preferably 15~45 weight %, still more preferably 30~40 weight %, in view of the resulting properties. In addition, when the above aqueous solution polymerization or reversed-phase suspension polymerization is carried out, a solvent other than water may be jointly used if necessary, and the kind of the solvent as jointly used is not especially limited.

When the above aqueous monomer solution is polymerized, one or more of the following radical polymerization initiators, for example, can be used: potassium persulfate, ammonium persulfate, sodium persulfate, t-butyl hydroperoxide, hydrogen peroxide, and 2,2'-azobis(2-aminodipropane) dihydrochloride.

Furthermore, a redox initiator is also available by further using a reductant to promote decomposition of the above polymerization initiator and combining both with each other. Examples of the above reductant include: (bi)sulfurous acid salts such as sodium sulfite and sodium hydrogensulfite; L-ascorbic acid (or its salts); reducible metals (or their salts) such as ferrous salts; and amines. However, the reductant is not especially limited to them.

The amount of the above polymerization initiator or reductant as used is usually in the range of 0.001~2 mol %, preferably 0.01~0.5 mol %, of the monomer component. In the case where the amount of the polymerization initiator is less than 0.001 mol %, there are disadvantages in that a large amount of monomer component remains unreacted, so the amount of the monomer, remaining in the resultant hydrophilic resin, increases. On the other hand, in the case where the amount of the polymerization initiator exceeds 2 mol %, there might be disadvantages in that the water-soluble content or coloring in the resultant hydrophilic resin, particularly, water-absorbent resin, increases.

In addition, the polymerization reaction may be carried out by irradiating the reaction system with active energy rays, such as radiations, electron beam, and ultraviolet rays, instead of or in combination with the use of the polymerization initiators. Incidentally, the reaction temperature in the above polymerization reaction is not especially limited, but is in the range of preferably 15~100° C., more preferably 20~90° C. In addition, the reaction time or pressure is not especially limited, either, and may fitly be determined according to factors such as the respective kinds of the monomer component and polymerization initiator and the reaction temperature.

Incidentally, in the polymerization, the following materials may be added to the reaction system: various foaming agents such as carbonates (or hydrogencarbonates), carbon dioxide, nitrogen, azo compounds, and inert organic solvents; hydrophilic polymers such as starch, cellulose, their derivatives, polyvinyl alcohol, polyacrylic acid (or its salts), and crosslinked polymers of polyacrylic acid (or its salts); various surface-active agents; and chain transfer agents such as hypophosphorous acid (or its salts).

When the aqueous solution polymerization is carried out, the resulting gel is preferably dried (after being disintegrated into fine pieces if necessary) and, if necessary, pulverized, classified, or further granulated, thus obtaining a hydrophilic resin. In the present invention, after the polymerization, the drying in as short a time as possible can give a hydrophilic resin which becomes still less colored. The water content in the hydrophilic resin is preferably at most 2%.

That is to say, when the hydrophilic resin is obtained in the present invention, its resin solid content as determined from the weight loss on drying (by heating 1 g of powder at 180° C. for 3 hours) is usually at least 80 weight %, preferably at least 85 weight %, more preferably at least 90 weight %, particularly preferably at least 95 weight %, further preferably at least 98 weight %, for achieving less coloring. In addition, the drying temperature is not especially limited, but is in the range of, for example, 100~300° C., preferably 150~250° C. In addition, the drying time is not especially limited, but leaving for a long time might bring about coloring, so the resin is dried to the above resin solid content in as short a time as possible, preferably within 5 hours, more preferably within 3 hours, particularly preferably within 1 hour, after the polymerization.

As to the drying method, the following various methods can be employed: heat drying; hot-air drying; drying under vacuum; infrared drying; microwave drying; drum drier drying; dehydration by azeotropy with hydrophobic organic solvents; and high-moisture drying by high temperature steaming. Thus, the drying method is not especially limited. However, the hot-air or high-moisture drying is preferable among the above-exemplified drying methods.

In the present invention, neither inert gas nor inert solvent is especially needed, and the hydrophilic resin which becomes little colored is obtainable under any atmosphere or drying condition, so the productivity or the resulting properties are excellent. In addition, the hot-air or high-moisture drying at high temperature in a short time is preferably applicable. In addition, although the dehydration by azeotropy with inert solvents at low temperature is used for drying in the reversed-phase suspension polymerization, commercially available water-absorbent resins as obtained by the reversed-phase suspension polymerization display somewhat low coloring that might be owing to the above particular drying. However, the dehydration by azeotropy is unfavorable because of the cost for the use of organic solvents or because of the safety worsening of the product by residual organic solvents. On the other hand, the method of the present invention is favorable in respect to not only the low coloring, but also the safety or low cost.

The shape of the hydrophilic resin as obtained in the present invention is not especially limited, and examples thereof include powdery such as irregular by pulverization or spherical, or gelatinous, sheet-shaped, bar-shaped, fibrous, or filmy. In addition, the hydrophilic resin may be combined with or carried on materials such as fibrous base materials. A hydrophilic resin, usable preferably for achieving the properties of the present invention, is a powdery one, particularly, an irregular pulverized one that conventionally displays high properties, but becomes outstandingly colored.

In view of the properties, the weight-average particle diameter of the powder of the hydrophilic resin is in the range of usually 10~2,000 $\mu$m, preferably 100~1,000 $\mu$m, more preferably 200~600 $\mu$m, and further, the content therein of fine particles of 150 $\mu$m or below is preferably as low as possible, more preferably 10 weight % or lower, still more preferably 5 weight % or lower. The present invention is particularly applicable to powders of coarse average particle diameter (for example, powder of which 50 weight % comprises particles of 300 $\mu$m or greater) or to powders with a low content of fine particles (for example, 150 $\mu$m or below), wherein these powders conventionally have problems of great coloring in spite of their high properties such as liquid-permeability or absorption capacity under a load. In addition, the substantial upper limit of the particle diameter is 850 $\mu$m or below, and the content of particles with a particle diameter of 850~300 $\mu$m in the entire powder is preferably at least 50 weight %, more preferably at least 70 weight %, particularly preferably at least 80 weight %.

In the present invention, the coloring can further be lessened by reducing the total content of hydroquinone and benzoquinone to 0.20 ppm or below and further by adjusting pH of the hydrophilic resin to a low value.

Among the above hydrophilic resins, those which have crosslinked structures can be water-absorbent resins. The water-absorbent resin absorbs a large quantity of, for example, water, a physiological salt solution, urine, and thereby swells to form a substantially water-insoluble hydrogel.

The water-absorbent resin in the present invention is typically obtained by polymerizing and crosslinking the monomer component and absorbs as large a quantity of water as 10~3,000 times its own weight in ion-exchange water and 5~200 times its own weight in a physiological salt solution to thereby form a water-insoluble hydrogel. In addition, examples of the above water-absorbent resin include those which have a water-soluble content of 25 weight % or below, preferably 15 weight % or below, more preferably 10 weight % or below, and are substantially water-insoluble. The shape of the water-absorbent resin is preferably a powder, more preferably a powder of the irregular pulverized shape, and its average particle diameter is also the same as that of the aforementioned hydrophilic resin.

The usable crosslinking process is not especially limited, and examples thereof include: (A) a process in which a hydrophilic polymer is obtained by polymerizing either one or both of acrylic acid and its salt or by copolymerizing therewith the above water-soluble unsaturated monomers, and then a crosslinking agent is added to the resultant hydrophilic polymer during or after the polymerization, thus post-crosslinking the hydrophilic polymer; (B) a process that involves radical crosslinking with radical polymerization initiators; and (C) a process that involves crosslinking by utilizing radiation such as electron beam. However, a preferable one is (D) a process in which a predetermined amount of internal-crosslinking agent is beforehand added to either one or both of acrylic acid and its salt, which might include the above water-soluble or hydrophobic unsaturated monomers as comonomers, and then polymerization is made, thus carrying out a crosslinking reaction simultaneously with or after the polymerization.

Examples of the internal-crosslinking agent, as used in the above process (D) include: N,N-methylenebisacrylamide, (poly)ethylene glycol di(meth)acrylate, (poly)propylene glycol di(meth)acrylate, (polyoxyethylene) trimethylolpropane tri(m eth)acrylate, trimethylolpropane di(meth) acrylate, polyethylene glycol di($\beta$-acryloyloxypropionate), trimethylolpropane tri($\beta$-acryloyloxypropionate), poly (meth)allyloxyalkanes, polyethylene glycol diglycidyl ether, ethylene glycol, polyethylene glycol, and glycerol. These internal-crosslinking agents may be used either alone respectively or in combinations with each other.

Incidentally, when one or more internal-crosslinking agents are used, it is preferable to essentially use a compound with two or more polymerizable unsaturated groups during the polymerization, considering the absorption properties of the resultant water-absorbent resin.

The amount of the above internal-crosslinking agent as used is preferably in the range of 0.005~2 mol %, more preferably 0.01~1 mol %, still more preferably 0.05~0.2 mol %, of the above monomer component. In the case where the amount of the internal-crosslinking agent is smaller than 0.005 mol % or where the amount of the internal-crosslinking agent exceeds 2 mol %, the desired absorption properties might not be obtained.

As to the water-absorbent resin of the present invention, it is preferable to regulate the total content of hydroquinone and benzoquinone to 0.20 ppm or below by adjusting pH of the water-absorbent resin itself in a physiological salt solution to 5.5 or below by fitly adjusting the monomer component, because the coloring of the water-absorbent resin can thereby further be lessened. Such an acid water-absorbent resin that displays pH of 5.5 or less in a physiological salt solution has an acid group as a functional group of the polymer and displays the acidity of pH of 5.5 or less in a physiological salt solution. Preferable examples of the acid group include carboxyl group, sulfonic acid group, sulfinic acid group, and phosphoric acid group. Hereinafter, the acid water-absorbent resin that displays pH of 5.5 or less in a physiological salt solution might simply be referred to as acid water-absorbent resin.

For the production of the acid water-absorbent resin, it is necessary (although it depends on the type or molar ratio of the monomer component as used) that when the monomer component including a major proportion of the monomer containing the above acid group (acid-group-containing monomer) is polymerized to obtain the water-absorbent resin, the pH of the resultant water-absorbent resin is adjusted so as to fall in the acid region of 5.5 or below by carrying out neither neutralization of the acid-group-containing monomer before or during the polymerization nor neutralization of the resultant water-absorbent resin, or by rendering the neutralization ratio of the acid group low, that is, carrying out what is called low neutralization.

When acrylic acid is used as the acid-group-containing monomer and when the acrylic acid salt is a sodium salt, it is preferable (although it depends on the type of the acrylic acid salt) to carry out the polymerization using acrylic acid of 100~58 mol % and the acrylic acid salt of 0~42 mol % (wherein the total of both is 100 mol %) as constituent units of the resultant polymer. In addition, when acrylic acid or its polymer is neutralized if necessary, this neutralization may be carried out to the monomer before polymerization, or by neutralization in which an acid or base is further added on the way of polymerization or after polymerization, that is, what is called post-neutralization. In these neutralizations, conventional inorganic or organic acids or bases are available.

The water-absorbent resin of the present invention may be a surface-crosslinked one.

The surface-crosslinking of the water-absorbent resin is to make a portion of high crosslinking density in a surface layer in addition to the uniform crosslinking structure inside the water-absorbent resin, and includes coating or impregnating the surface of the water-absorbent resin with the below-mentioned surface-crosslinking agent. That is to say, the surface-crosslinking of the water-absorbent resin (as obtained using either one or both of acrylic acid and its salt which merely have a content of at most 0.20 ppm in total of hydroquinone and benzoquinone) can give a new surface-crosslinked water-absorbent resin which displays little coloring with time as has never been obtained (hereinafter, this surface-crosslinked water-absorbent resin might be referred to as water-absorbing agent).

The surface-crosslinking of the water-absorbent resin enhances the absorption capacity under a load. Water-absorbent resins of high absorption capacity under a load among conventional ones on the market are known, but any of them becomes colored with time and therefore actually cannot be used for diapers or napkins of high core concentration to which attention is paid in recent years. The water-absorbing agent of the present invention merely has a coloring degree (YI) of at most 20 after being left for 1 week, and thus displays little coloring, and further, has an absorption capacity of at least 20 g/g for a physiological salt solution under a load (50 g/cm$^2$). The absorption capacity under a load of the water-absorbing agent is usually at least 20 g/g, preferably at least 23 g/g, more preferably at least 25 g/g.

Examples of the surface-crosslinking agent, usable in the present invention, include: polyhydric alcohol compounds such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymer, pentaerythritol and sorbitol; epoxy compounds such as ethylene glycol diglycidyl ether, polyethylene diglycidyl ether, glycerol polyglycidyl ether, diglycerol polyglycidyl ether, polyglycerol polyglycidyl ether, propylene glycol diglycidyl ether, polypropylene glycol diglycidyl ether and glycidol; polyamine compounds, such as ethylenediamine, diethylenetriamine, triethylenetetraamine, tetraethylenepentaamine, pentaethylenetetraamine, polyethylenimine, and polyamide-polyamine; haloepoxy compounds, such as epichlorohydrin, epibromohydrin and α-methylepichlorohydrin; condensation products from the above polyamine compounds and the above haloepoxy compounds; polyisocyanate compounds such as 2,4-tolylene diisocyanate and hexamethylene diisocyanate; polyoxazoline compounds such as 1,2-ethylenebisoxazoline; silane coupling agents such as γ-glycidoxypropyltrimethoxysilane and γ-aminopropyltrimethoxysilane; and alkylene carbonate compounds such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxapan-2-one. However, the surface-crosslinking agent is not especially limited. The above-exemplified surface-crosslinking agents are usable regardless of pH.

In view of the resulting properties or coloring, preferable ones among the above-exemplified surface-crosslinking agents are polyhydric alcohols, epoxy compounds, polyamine compounds, condensation products from polyamine compounds and haloepoxy compounds, and alkylene carbonate compounds.

Particularly, the present inventors found that the crosslinking reaction needs high temperature and relatively easily colors with time. Preferable surface-crosslinking agents are dehydratable surface-crosslinking agents (such as polyamines, polyhydric alcohols, alkylene carbonates), and particularly, polyhydric alcohols are favorably usable in view of the resulting properties or coloring in the present invention.

Incidentally, in view of the resulting properties, it is permissible in the present invention that the polyhydric alcohol is not reacted, but used as a solvent for other surface-crosslinking agents, thus impregnating the surface of the water-absorbent resin with the polyhydric alcohol. In the case where the polyhydric alcohol is not used as a solvent or surface-crosslinking agent for water-absorbent resins (particularly, acid water-absorbent resins), no water-absorbing agent that is particularly fit to diapers for adults or to sanitary napkins might be obtainable for the following reason: the absorption capacity under a load is not enhanced, and further, the residue of the surface-crosslinking agent is seen, or the water absorption speed greatly falls, or inferior results are provided with regard to the miscibility of the fibrous base material and the water-absorbing agent or to the core shape retention ability.

In addition, when the surface-crosslinking is carried out to the above acid water-absorbent resin, the polyhydric alcohol (as the solvent or surface-crosslinking agent) is particularly effective to the surface-crosslinking of the acid water-absorbent resin. It is new finding by the present inventors that: because the acid water-absorbent resin displays slow water absorption speed and low Tg during the surface-crosslinking and has high tackiness, its uniform surface-crosslinking is difficult, so the polyhydric alcohol (as the solvent or surface-crosslinking agent, particularly, as the surface-crosslinking agent) is needed for improving the surface-crosslinking, water absorption speed, or core shape retention ability of the acid water-absorbent resin. In addition, the inventors further found that the polyhydric alcohol to impregnate or crosslink the surface of the water-absorbing agent with is further important for preventing the acid water-absorbent resin from directly touching skin.

As is proposed in JP-A-06-184320 (U.S. Pat. No. 5,422,405), also when the surface-crosslinking agent (which is used for the surface-crosslinking of the water-absorbent resin and can react upon the carboxyl group) comprises a combination of a first surface-crosslinking agent and a second surface-crosslinking agent whose solubility parameters are deferent from each other, a water-absorbing agent with still more excellent absorption capacity under a load can be obtained.

The above solubility parameter is a value as commonly used as a factor indicating the polarity of compounds. The solubility parameters, σ $(cal/cm^3)^{1/2}$, of solvents, as disclosed on pages 527–539 of *Polymer Handbook*, 3 rd edition, published by WILEY INTERSCIENCE, are applied to the above-mentioned solubility parameter in the present invention. In addition, values, as applied to solubility parameters of solvents as not disclosed on the above-mentioned pages, are led by substituting Hoy's cohesive energy constant, as disclosed on page 525 of the *Polymer Handbook* above, for Small's equation as disclosed on page 524 of the *Polymer Handbook* above.

The above-mentioned first surface-crosslinking agent is preferably a compound which is reactive upon the carboxyl group and has a solubility parameter of at least 12.5 $(cal/cm^3)^{1/2}$, more preferably at least 13.0 $(cal/cm^3)^{1/2}$. The above-mentioned second surface-crosslinking agent is preferably a compound which is reactive upon the carboxyl group and has a solubility parameter less than 12.5 $(cal/cm^3)^{1/2}$, more preferably in the range of 9.5 to 12.0 $(cal/cm^3)^{1/2}$. Examples of the first surface-crosslinking agent include propylene glycol and glycerol, and examples of the second surface-crosslinking agent include ethylene glycol diglycidyl ether and butanediol.

The amount of the surface-crosslinking agent, as used, is different according to the compounds as used as such, or to combinations thereof, but is in the range of preferably 0.001 to 10 weight parts, more preferably 0.01 to 5 weight parts, per 100 weight parts of the solid content of the water-absorbent resin.

In addition, when the surface-crosslinking agents are jointly used, it is preferable that one of them is a polyhydric alcohol. In addition, the amount of the polyhydric alcohol (which prevents the acid water-absorbent resin from directly touching skin and is used as the surface-crosslinking agent or solvent) is in the range of preferably 0.01 to 10 weight parts, more preferably 0.1 to 10 weight parts, still more preferably 0.2 to 5 weight parts, particularly preferably 0.5 to 4 weight parts, per 100 weight parts of the solid content of the water-absorbent resin.

For improving the absorption capacity under a load, it is preferable that the surface-crosslinking agent in the present invention contains water as a solvent. The amount of water, as used, is different according to factors such as the kind, particle diameter, or water content of the water-absorbent resin, but is in the range of preferably 0~20 weight parts (but not including zero), more preferably 0.5~10 weight parts.

In addition, the surface-crosslinking agent in the present invention may further contain a hydrophilic organic solvent (aqueous liquid) if necessary. Examples thereof include: lower alcohols, such as methyl alcohol, ethyl alcohol, n-propyl alcohol, isopropyl alcohol, n-butyl alcohol, isobutyl alcohol, and t-butyl alcohol, or EO adducts of these alcohols; ketones such as acetone; ethers such as dioxane and tetrahydrofuran; amides such as N,N-dimethylformamide; and sulfoxides such as dimethyl sulfoxide. The amount of the hydrophilic organic solvent as used is different according to factors such as the kind, particle diameter, or water content of the water-absorbent resin, but is preferably 20 weight parts or below, more preferably in the range of 0.1~10 weight parts, per 100 weight parts of the solid content of the water-absorbent resin for the purpose of improving its absorption capacity under a load.

The mixing of the water-absorbent resin with the surface-crosslinking agent or its solution or dispersion may be carried out by directly spraying or dropping the surface-crosslinking agent or its solution or dispersion to the water-absorbent resin, or by dispersing the water-absorbent resin into a large quantity of dispersion solvent of about 50~about 5,000 weight % (relative to the water-absorbent resin).

The water-absorbent resin and the surface-crosslinking agent are mixed (if necessary, the heating treatment may further be carried out) to crosslink the neighborhood of the surface of the water-absorbent resin, thus obtaining a water-absorbing agent having an absorption capacity of 20 g/g or more for a physiological salt solution under a load of 50 g/cm$^2$. On this occasion, it is preferable to adjust pH of the starting water-absorbent resin to 5.5 or below, because the coloring can thereby further be prevented.

That is to say, considering the reactivity of the surface-crosslinking agent, the simplicity of the production apparatus, and the productivity, it is preferable to carry out heating-treatment to react the surface-crosslinking agent in the neighborhood of the surface of the water-absorbent resin. In view of not only the resulting properties or productivity but also the further prevention of the coloring, it is preferable to carry out the reaction in a short time in a dried state, and it is therefore preferable to carry out the heat crosslinking of the neighborhood of the surface in the powder system and at a temperature of 100~250° C. within 3 hours. Incidentally, the powder system is to carry out the reaction by directly adding the crosslinking agent to a dry water-absorbent resin using substantially no dispersion solvent for the water-absorbent resin.

The heating temperature at which the above heating treatment is carried out is in the range of preferably 100~250° C., more preferably 150~250° C. In addition, the heating time is preferably determined in the range of 1 minute to 2 hours, and more preferably, for example, 0.1~1.5 hours at 180° C., and 0.1~1 hour at 200° C. The heating treatment can be carried out using conventional dryers or heating-furnaces. Examples of the dryers include: channel type mixing dryers, rotary dryers, desk dryers, fluidized-bed dryers, gas-stream type dryers, and infrared dryers.

In addition, in the present invention, because the water-absorbent resin having little content in total of hydroquinone and benzoquinone is used, the coloring that accompanies the surface-crosslinking can be prevented, and further, the coloring with time of the resultant water-absorbent resin can also be prevented. In addition, it was found that: if an acid water-absorbent resin is used, the coloring can be more prevented, and further when the polyhydric alcohol is used as the surface-crosslinking agent, its reactivity is greatly enhanced, whereby not only is the productivity improved, but also the thermal degradation of the water-absorbent resin is avoidable.

In the above surface-crosslinking, the adjustment of the surface-crosslinking agent or heating treatment conditions (temperature or time) can give an absorption capacity of 20 g/g or more under a load and a water absorption capacity of preferably 25 g/g or more under no load.

The water-absorbing agent of the present invention as obtained in the above way is a new water-absorbing agent with properties as have never been achieved, namely, a water-absorbing agent which is crosslinked with surface-crosslinking agents such as polyhydric alcohols and has an absorption capacity of 20 g/g or more for a physiological salt solution under a load of 50 g/cm$^2$. In addition, the water-absorbing agent of the present invention is a water-absorbing agent which has an absorption capacity of 20 g/g or more under a load and merely has a coloring degree (YI) of at most 20 after being left under conditions of the open system, 70° C., 65% RH for 1 week. In addition, as to the water-absorbing agent, the shape is preferably an irregular pulverized one, and the particle diameter is as above.

The water-absorbing agent of the present invention displays an absorption capacity of preferably at least 30 g/g for a physiological salt solution under a load of 20 g/cm$^2$ and further an extremely high value of an absorption capacity of preferably at least 25 g/g, more preferably at least 30 g/g, for artificial urine under a heavy load (50 g/cm$^2$). The absorption capacity under no load of the water-absorbing agent is preferably at least 25 g/g, more preferably at least 28 g/g. In addition, as to the water-absorbing agent, the shape is preferably powdery, and the average particle diameter is as above. The water-soluble content or preferable YI value or its change ($\Delta$YI) in the water-absorbing agent is also preferably in the aforementioned range.

Particularly for the purpose of obtaining a low-coloring water-absorbent resin, the excessive acidity (strong acidity) might deteriorate the properties or stimulate skin even if the crosslinking agent is used, so pH of the water-absorbing agent is in the range of preferably 5.3~2.8, more preferably 5.3~4.5, particularly preferably in the weak acid region of 5.3~4.8.

Furthermore, the water-absorbing agent of the present invention displays little coloring for a long time even under high temperature and high humidity (for example, 70° C./65% RH), and is therefore fit for the use or preservation at a temperature of 25° C. or higher under relative humidity of 65% or higher.

In addition, when pH of the starting water-absorbent resin is adjusted to 5.5 or below, the water-absorbing agent of the present invention (particularly, that which is surface-crosslinked or surface-impregnated with the polyhydric alcohol) usually displays a blocking ratio of at most 50 weight % when left under conditions of 25° C., relative humidity 60% for 2 hours and is therefore excellent in the hygroscopic fluidity (blocking resistance of the water-absorbing agent under high humidity). The blocking ratio of the water-absorbing agent of the present invention is preferably at most 30 weight %, more preferably at most 20 weight %, particularly preferably at most 10 weight %.

It is widely known that acid water-absorbent resins of low neutralization ratio, for example, have the following problems: the increase in the tackiness of the resin; Tg depression; water absorption speed depression; and the volatility of the monomer. Therefore, conventional water-absorbent resins are substantially neutral ones (pH=6~8, or about 6.1, to which almost all commercially available ones for sanitary materials correspond), for example, neutral polyacrylic acid salt crosslinked products with the neutralization ratio of about 65~about 90%, considering uses as sanitary materials, and further, particularly because of ease of the surface-crosslinking.

However, the present inventors found that: unexpectedly, water-absorbing agents, as obtained by surface-crosslinking the above acid water-absorbent resins with surface-crosslinking agents such as polyhydric alcohols, display little coloring, and involve the improved surface-crosslinking reactivity (productivity) and the decreased monomer residue, and have the improved hygroscopic fluidity (blocking resistance) or liquid diffusibility and excellent deodorizability, and is fit for absorbent articles, particularly, sanitary napkins or disposable diapers for adults. In the present invention, particularly, as pH of the water-absorbent resin is depressed, the change of the coloring degree ($\Delta YI$) with time can be decreased. Therefore, even only 0~10 mol % neutralized, furthermore, substantially unneutralized, polyacrylic acid crosslinked products are favorably usable.

It is conventionally known to add additives such as inorganic powders or surfactants to the water-absorbent resin to improve its hygroscopic fluidity, but these additives have not only problems of the safety or cost, but also problems in that they deteriorate the properties (e.g. absorption capacity under a load) of the water-absorbent resin or the water absorption actions (e.g. miscibility or bindability to pulp or the liquid desorption (wet back)) of the water-absorbent resin in absorbent articles including the water-absorbent resin. In comparison therewith, by a simple means of acidifying pH, the water-absorbing agent of the present invention displays the surprising improvement in the hygroscopic fluidity, and involves the decreased monomer residue and the improved surface-crosslinking reactivity, and further, does not influence the properties, cost, or safety.

Various functions also can be given to the water-absorbent resin or water-absorbing agent of the present invention by adding thereto the following materials: disinfectants; antimicrobial agents; perfumes; various inorganic or organic powders; foaming agents; pigments; dyes; hydrophilic short fibers; manure; oxidants; reductants; water; salts; various hydrophilic resins other than the present invention polyacrylic acids; or various hydrophobic resins. The amount of these additives is fitly determined according to the purpose, but is, for example, 0.001~400 weight % of the water-absorbent resin or water-absorbing agent of the present invention.

Next, an explanation is made on the absorbent article of the present invention.

The absorbent article of the present invention comprises: an absorbent layer including the present invention water-absorbent resin and a fibrous base material; a liquid-permeable surface sheet; and a liquid-impermeable back sheet; wherein the weight ratio, $\alpha$, of the water-absorbent resin to the total of the water-absorbent resin and the fibrous base material is 0.3 or more. The weight ratio $\alpha$ is in the range of preferably 0.4~1.0, more preferably 0.5~0.8.

In the case where the above weight ratio $\alpha$ is less than 0.3, the amount of the water-absorbent resin is small to give an absorbent article having a relatively uniform distribution of the water-absorbent resin regardless of the type of the resin, but the resultant absorbent article is generally bulky and displays much desorption (wet back). Particularly, the use of the present invention water-absorbent resin is very preferable, because this resin displays very little coloring in the initial stage and with time after being produced, and therefore has no problem of coloring even if the water-absorbent resin is combined in a high concentration of $\alpha$ of 0.3 or more.

In a production process for this absorbent article, the water-absorbent resin is blended or sandwiched with the fibrous base material to prepare an absorbent structure (absorbent core), and the resultant absorbent core is sandwiched between a liquid-permeable surface material and a liquid-impermeable base material, and the resultant product is, if necessary, provided with materials such as an elastic member, a diffusion layer, or a pressure sensitive tape, thus obtaining an absorbent article, particularly, sanitary napkin or diaper for adults. The above absorbent core is subjected to compression forming so as to have a density of 0.06~0.5 g/cc and a basis weight of 0.01~0.20 g/cm$^2$. Incidentally, the usable fibrous base material is preferably a hydrophilic fiber, for example, pulverized wood pulp, and other examples include cotton linters, crosslinked cellulose fibers, rayon, cotton, wool, acetate, vinylon. Preferably, they may be air-laid.

Even when the resin concentration is high such that the weight ratio $\alpha$ of the water-absorbent resin to the total of the water-absorbent resin and the fibrous base material is 0.3 or more, the use of the present invention water-absorbent resin enables the production with good workability of an absorbent structure in which the fiber and the resin are uniformly blended.

Thus, the present invention water-absorbent resin can stably provide an absorbent article that has high resin concentration and displays excellent absorption properties. Specific examples of such an absorbent article include sanitary materials such as disposable diapers for adults, which greatly develop in recent years, diapers for children, sanitary napkins, and so-called incontinent pads, but there is no especial limitation. The water-absorbent resin, as included in the absorbent article, has excellent working and mixing properties and is excellent in the absorption capacities under a load (e.g. liquid permeability, absorption amount, diffusibility, absorption speed), so the absorbent article displays little desorption (wet back) and therefore gives great dry feeling, whereby the burden on wearers of the absorbent article or on people who take care of the wearers can greatly be lessened.

The hydrophilic or water-absorbent resin of the present invention is favorable for the use or preservation under high humidity, particularly, under conditions of 25° C. or higher, relative humidity of 50% or higher, and is preferably usable with no especial humidity adjustment in any factory environment. Particularly, it is more preferable to use the water-absorbent resin in a powdered state, because the powdery water-absorbent resin according to the present invention displays little blocking or coloring even under high humidity.

In addition, the present invention further provides a coloring evaluation method of a hydrophilic resin, which comprises the step of judging the coloring degree that the hydrophilic resin displays when left under conditions of the open system, a certain temperature, and a certain humidity. The temperature and the humidity are preferably a temperature of 25° C. or higher and a humidity of 50% or higher, and more preferably a temperature of 40~100° C. and a humidity of 60~100%. In addition, the time as needed for the evaluation is preferably 12 hours or longer, more preferably 24~480 hours. When compared with a conventional coloring evaluation method in the closed system as disclosed in JP-A-05-086251, that of the present invention is simple and accurate, and more corresponds to actual coloring.

(Effects and Advantages of the Invention):

The present invention can provide a hydrophilic resin which displays little coloring or discoloring even when preserved for a long time, because acrylic acid for polymerization which has little content in total of hydroquinone and benzoquinone as a starting material.

The present invention further provides a hydrophilic resin which contains a quinhydronation inhibitor. This hydrophilic resin also displays little coloring or discoloring even when preserved for a long time.

The hydrophilic resin of the present invention merely has a coloring degree (YI) of at most 20 after being left under conditions of the open system, 70° C., 65% RH for 1 week, so this resin displays little coloring or discoloring even when preserved for a long time.

The water-absorbent resin, among the hydrophilic resins of the present invention, absorbs various liquids such as water, body fluids, a physiological salt solution, urine, blood, cement water, and water containing manure, and is usable for absorbent articles, if necessary, in combination with base materials such as nonwoven fabrics, films, and pulp. Such absorbent articles are useful for various industrial purposes, which need water-absorption, water-holding, wetting, swelling, and gelation, for example, as follows: articles contacting human bodies, such as disposable diapers, sanitary napkins, and incontinent pads; materials to separate water from oil; other dehydrating or drying agents; water-holding materials for plants or soil; solidifiers for muddy sediment; dewfall preventives; water-cutting-off materials for electric wires or optical fibers; and water-cutting-off materials for engineering works or buildings.

The hydrophilic resin of the present invention can be applied to all conventional uses of all hydrophilic resins (e.g. water-soluble resins) other than water-absorbent resins. For example, as to uses of builders for liquid detergents or uses of pressure sensitive adhesives, the coloring or discoloring degrades the goods value, so it is effective to use the hydrophilic resin of the present invention.

In addition, the water-absorbent resin of the present invention is widely applicable to uses of various conventional water-absorbent resins, for example, absorbent articles such as diapers for children and incontinent pads. Particularly, if this water-absorbent resin is surface-crosslinked with the polyhydric alcohol and if a water-absorbent resin with pH of 5.5 or below is used as a starting material, the resultant surface-crosslinked water-absorbent resin has excellent blocking resistance and is usable even for purposes, such as sanitary napkins and diapers for adults, for which it has been assumed so far that there is no fit water-absorbent resin.

In the preservation period, the absorbent article comprising the water-absorbent resin of the present invention does not color or discolor, and therefore does not degrade its value as goods.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited to the below-mentioned examples.

In addition, in the examples, unless otherwise noted, "part(s)" denotes "weight part(s)."

The properties ①–⑧, as recited in the appended claims and the below-mentioned examples of some preferred embodiments, were determined by the following measurement methods.

① Quantification Method of Total of Hydroquinone and Benzoquinone:

The total content of hydroquinone and benzoquinone in purified acrylic acid was quantified by a coloring method as follows.

(1) First, 10 ml of deionized water is placed with a whole pipette into a measuring flask of 25 ml in capacity, to which 2 ml of a sample solution is then added.

(2) As the blank, 10 ml of deionized water is placed with a whole pipette into a measuring flask of 25 ml in capacity.

(3) After both liquids are cooled with ice for 15 minutes, 5 ml of n-butylamine as beforehand cooled with ice for 30 minutes is added thereto with a whole pipette, and they are mixed by stirring in ice water to react them until white smoke disappears.

(4) After the total amount of the reaction mixture is increases to 25 ml by dilution with deionized water, the absorbance was measured with a spectrophotometer (model 100-40 made by Hitachi Seisakusho Co., Ltd.) to quantify hydroquinone.

② Method to Evaluate Coloring with Time of Water-absorbent Resin:

First, 2.000 g of water-absorbent resin (dry powder: unless otherwise noted, dry powder of 600~300 μm in particle diameter) was spread on the bottom of a polypropylene vessel (120 cc, Pack-Ace made by Teraoka Co., Ltd.) of 55 mm in inner diameter and 70 mm in height, and then the water-absorbent resin powder was left at 70° C. under 65% RH atmosphere for 1 week in a thermo-humidistat (PLATINOUS LUCIFER, model No. PL-2 G made by Tabai Especk Co., Ltd.) in the open system with no cap on the vessel. Incidentally, the amount per unit area of the above water-absorbent resin as spread, 0.084 g/cm$^2$, is a model amount in the high concentration core.

After 1 week, the entirety of the water-absorbent resin in the vessel was filled into the below-mentioned powder-paste sample cell (30 mm φ), and the surface color of the water-absorbent resin was measured in terms of the coloring degree (YI value) with a spectral color difference meter, SZ-Σ80 COLOR MEASURING SYSTEM (made by Nippon Denshoku Kogyo Co., Ltd.), under the setting conditions (reflection measurement; powder-paste sample cell (30 mm φ) as the attachment; standard circular white plate No 2 for powder-paste as the standard; 30 φ floodlight pipe).

③ Measurement Method of Absorption Capacity of Water-absorbent Resin:

First, 0.2 g of water-absorbent resin was uniformly placed into a nonwoven-fabric-made tea bag type bag (40×150 mm) and then immersed into a 0.9 wt % aqueous sodium chloride solution (physiological salt solution). Thirty minutes later, the bag was drawn up and then drained for a predetermined time, and the weight $W_1$ of the bag was then measured. On the other hand, the same procedure was carried out using no water-absorbent resin, and the resultant weight $W_2$ was measured. Thus, the absorption capacity was calculated in accordance with the following equation:

absorption capacity (g/g)=(weight $W_1$(g) after absorption–blank weight $W_2$(g))/(weight (g) of water-absorbent resin).

④ pH in Physiological Salt Solution

First, 100 mg of water-absorbent resin or water-absorbing agent is added to 100.0 g of physiological salt solution (room temperature: 23±2° C.) in a glass beaker containing a stirring rod of 300 rpm, and then stirred for 20 minutes. Then, pH of the physiological salt solution, in which the resultant swollen gel is dispersed, is measured with a pH meter (glass-electrodic hydrogen ion concentration type; made by Horiba Seisakusho Co., Ltd.).

⑤ Water-soluble Content and Residual Monomer

First, 0.50 g of water-absorbent resin or water-absorbing agent was dispersed into 1,000 ml of deionized water and then stirred with a magnetic stirrer for 16 hours. Then, the resultant swollen gel was separated and filtrated with a filter paper (TOYO, No. 6). Next, the weight percentage (relative to the water-absorbent resin) of the water-soluble content in the water-absorbent resin was determined by carrying out colloidal titration of water-soluble polymers as eluted from the water-absorbent resin into the filtrate. In addition, separately, the filtrate of the water-absorbing agent, as stirred for 2 hours, was UV-analyzed by liquid chromatography to determine the amount (ppm relative to the water-absorbing agent) of monomer remaining in the water-absorbing agent.

⑥ Absorption Capacity Under Load:

Hereinafter, the measurement apparatus as used for measuring the absorption capacity under a load is explained while referring to FIG. 1.

As is shown in FIG. 1, the measurement apparatus comprises: a scale 1; a vessel 2 of a predetermined capacity as mounted on the scale 1; an air-inhaling pipe 3; an introducing tube 4; a glass filter 6; and a measurement part 5 as mounted on the glass filter 6. The vessel 2 has an opening part 2a on the top and an opening part 2b on the side. The air-inhaling pipe 3 is inserted in the opening part 2a, and the introducing tube 4 is fitted to the opening part 2b.

In addition, the vessel 2 contains a predetermined amount of physiological salt solution 11 or artificial urine. The lower end part of the air-inhaling pipe 3 is submerged in the physiological salt solution 11. The air-inhaling pipe 3 is set to keep the internal pressure of the vessel 2 nearly atmospheric. The glass filter 6 is formed in a diameter of 55 mm. The vessel 2 and the glass filter 6 are connected to each other through the introducing tube 4 made of silicone resin. In addition, the position and level of the glass filter 6 are fixed relative to the vessel 2.

The measurement part 5 comprises: a filter paper 7; a supporting cylinder 8; a wire net 9 as attached to the bottom of the supporting cylinder 8; and a weight 10; and the measurement part 5 is formed by mounting the filter paper 7 and the supporting cylinder 8 (with the wire net 9 at the bottom) in this order on the glass filter 6 and further mounting the weight 10 inside the supporting cylinder 8, namely, on the wire net 9. The wire net 9 is made of stainless steel and formed in 400 mesh (mesh size: 38 µm according to JIS). The level of the upper face of the wire net 9, namely, of the contact face of the wire net 9 with the water-absorbent resin, is set so as to be as high as the level of the lower end face of the air-inhaling pipe 3. An arrangement is made such that a predetermined amount of water-absorbent resin with a predetermined particle diameter can uniformly be spread on the wire net 9. The weight 10 is adjusted in weight such that a load of 20 g/cm$^2$ or 50 g/cm$^2$ can uniformly be applied to the water-absorbent resin on the wire net 9.

The absorption capacity under a load was measured with the measurement apparatus having the above-mentioned constitution. The measurement method is hereinafter explained.

First, predetermined preparatory operations are made such that a predetermined amount of 0.9 weight % physiological salt solution 11 is placed into the vessel 2, and that the air-inhaling pipe 3 is inserted into the vessel 2. Next, the filter paper 7 is mounted on the glass filter 6, and in parallel with this mounting operation, 0.9 g of water-absorbent resin is uniformly spread inside the supporting cylinder 8, namely, on the wire net 9, and the weight 10 is put on this water-absorbent resin. Next, the wire net 9 (on which the water-absorbent resin and the weight 10 are mounted) of the supporting cylinder 8 is mounted on the filter paper 7 such that the center line of the wire net 9 will conform with that of the glass filter 6.

Then, the weight of the physiological salt solution 11, as absorbed by the water-absorbent resin over a period of 60 minutes since the supporting cylinder 8 was mounted on the filter paper 7, is determined from a value as measured with the scale 1. In addition, the same procedure as the above is carried out using no water-absorbent resin, and the weight of the physiological salt solution, as absorbed by materials other than the water-absorbent resin, such as the filter paper 7, is determined from a value as measured with the scale 1 and regarded as the blank value. Next, the weight of the physiological salt solution 11, as actually absorbed by the water-absorbent resin, is determined by correction by subtracting the blank value and then divided by the weight of the water-absorbent resin (0.9 g), thus calculating the absorption capacity under a load of 20 g/cm$^2$ or 50 g/cm$^2$.

In the measurement, besides the physiological salt solution (0.9 wt % aqueous NaCl solution), artificial urine was separately used as the liquid to be absorbed. The artificial urine as used for the measurement was prepared by dissolving sodium sulfate, potassium chloride, magnesium chloride hexahydrate, calcium chloride dihydrate, ammonium dihydrogenphosphate, and diammonium hydrogenphosphate in the concentrations of 0.2 weight %, 0.2 weight %, 0.05 weight %, 0.025 weight %, 0.085 weight %, and 0.015 weight % respectively into deionized water.

⑦ Hygroscopic Blocking Ratio:

First, 2.000 g of water absorbent resin powder, as passed a screen of JIS 850 µm, was uniformly spread on the bottom of an aluminum cup (bottom diameter: 52 mm/height: 22 mm) and placed into a thermo-humidistat (PLATINOUS LUCIFER PL-2 G made by Tabai Especk Co., Ltd.) of 25° C. in temperature and 60% in relative humidity. Next, after being left for 2 hours, the water-absorbent resin was got out of the thermo-humidistat, and then the entirety of the water-absorbent resin in the aluminum cup was moved to a JIS standard sieve of 7.5 cm in diameter and of 2,000 µm in mesh size and left on the sieve without vibration.

Then, the weight (g) of the water-absorbent resin remaining on the 2,000-µm sieve and the weight (g) of the water-absorbent resin as passed the sieve were measured, and the ratio between these weights ((water-absorbent resin (g) on sieve)/((water-absorbent resin (g) on sieve)+(water-absorbent resin (g) as passed sieve))) was calculated to determine the blocking ratio (%) of the water-absorbent resin. Of course, a water-absorbent resin displaying a lower blocking ratio is a preferable water-absorbent resin that is more excellent in the fluidity after absorbing the moisture.

⑧ Hygroscopicity:

In test ⑦ above, the hygroscopicity (weight % relative to the water-absorbent resin) was determined by determining the increase in the weight (0.1 mg unit) of the water-absorbent resin as displayed when 2.000 g of water absorbent resin powder was allowed to absorb the moisture for 2 hours under conditions of the thermo-humidistat (PLATINOUS LUCIFER PL-2 G made by Tabai Especk Co., Ltd.) of 25° C. in temperature and 60% in relative humidity. Of course, in view of the preservation stability as the water-absorbent resin, it is preferable that the hygroscopicity (%) is small.

EXAMPLE 1

(Acrylic Acid Having a Content of 0.15 ppm in Total of HQ and BQ (Hydroquinone and Benzoquinone))

When the resultant reaction gas was absorbed by water in an absorption column in a process of producing acrylic acid by catalytic gas phase oxidation of propylene, hydroquinone was added to and absorbed by the absorption liquid such that the hydroquinone content of the resulting aqueous acrylic acid solution would be 300 ppm, thus obtaining an aqueous acrylic acid solution. Next, low boiling fractions such as acetic acid and propionic acid were distilled off from this aqueous acrylic acid solution, and further, high boiling fractions such as dimers of acrylic acid or maleic acid were then removed, thus obtaining crude acrylic acid. The composition of this crude acrylic acid was as follows: acrylic acid 99.75 weight %, acetic acid 0.07 weight %, propionic acid 0.05 weight %, water 0.05 weight %, others 0.08 weight %, and the total content of hydroquinone and benzoquinone was 10 ppm.

The resultant crude acrylic acid was purified by the following process using a simple distillation apparatus, thus obtaining purified acrylic acid (a). First of all, hydroquinone was added as the polymerization inhibitor to the crude acrylic acid such that the total content of hydroquinone and benzoquinone therein would be 500 ppm. Then, while the resultant mixture was continuously supplied to a column bottom of the distillation apparatus at 1,000 g/hr, distillation was carried out under decompression of 50 mmHg to continuously extract purified acrylic acid and waste oil at 985 g/hr and 15 g/hr respectively. The composition of the resultant waste oil was as follows: acrylic acid 50.6 weight %, acetic acid 0.01 weight %, propionic acid 0.01 weight %, and others 49.3 weight %; and the composition of the resultant purified acrylic acid (a) was as follows: acrylic acid 99.83 weight %, acetic acid 0.07 weight %, propionic acid 0.05 weight %, water 0.05 weight %, and the total content of hydroquinone and benzoquinone was 0.15 ppm. Next, 1754.5 g of ion-exchange water was put into a distillation flask as equipped with a stirrer, and then 1,280 g of purified acrylic acid (a) and 1,482 g of a 48 weight % aqueous sodium hydroxide solution were dropped into the flask while the temperature in the flask was kept at 20~40° C., thus obtaining purified sodium acrylate (b) as a 37 weight % aqueous solution.

EXAMPLE 2

(Acrylic Acid Having a Content of 0.15 ppm in Total of HQ and BQ)

Purification was carried out with a crystallization apparatus in the following way as a purification process of crude acrylic acid. Hydroquinone was added as the polymerization inhibitor to crude acrylic acid, as obtained in the same way as of Example 1, such that the total content therein of hydroquinone and benzoquinone would be 500 ppm. Then, 10,000 g of the resultant mixture was introduced into the crystallization apparatus, thus obtaining 9,850 g of purified acrylic acid (c).

The composition of the resultant waste oil was as follows: acrylic acid 81.9 weight %, acetic acid 4.0 weight %, propionic acid 2.7 weight %, water 2.7 weight %, and others 8.7 weight %; and the composition of the resultant purified acrylic acid (c) was as follows: acrylic acid 99.97 weight %, acetic acid 0.01 weight %, propionic acid 0.01 weight %, water 0.01 weight %, and the total content of hydroquinone and benzoquinone was 0.10 ppm. Purified acrylic acid (c) was neutralized in the same way as of Example 1, thus obtaining purified sodium acrylate (d) as a 37 weight % aqueous solution.

COMPARATIVE EXAMPLE 1

(Acrylic Acid Having a Content of 1.20 ppm in Total of HQ and BQ)

Purified acrylic acid (e) was obtained with the same distillation apparatus as of Example 1 in the following way as a purification process of crude acrylic acid. Hydroquinone was added as the polymerization inhibitor to crude acrylic acid, as obtained in the same way as of Example 1, such that the total content therein of hydroquinone and benzoquinone would be 1,500 ppm. Then, while the resultant mixture was continuously supplied to a column bottom of the distillation apparatus at 1,000 g/hr, distillation was carried out under decompression of 50 mmHg to continuously extract purified acrylic acid and waste oil at 985 g/hr and 15 g/hr respectively.

The composition of the resultant waste oil was as follows: acrylic acid 49.9 weight %, acetic acid 0.01 weight %, propionic acid 0.01 weight %, and others 50.0 weight %; and the composition of the resultant purified acrylic acid (e) was as follows: acrylic acid 99.82 weight %, acetic acid 0.01 weight %, propionic acid 0.05 weight %, water 0.06 weight %, and the total content of hydroquinone and benzoquinone was 1.20 ppm. Purified acrylic acid (e) was neutralized in the same way as of Example 1, thus obtaining purified sodium acrylate (f) as a 37 weight % aqueous solution.

COMPARATIVE EXAMPLE 2

(Acrylic Acid Having a Content of 1.10 ppm in Total of HQ and BQ)

Purified acrylic acid (g) was obtained with the same crystallization apparatus as of Example 2 in the following way as a purification process of crude acrylic acid. Hydroquinone was added as the polymerization inhibitor to crude acrylic acid, as obtained in the same way as of Example 1, such that the total content therein of hydroquinone and benzoquinone would be 1,500 ppm. Then, 10,000 g of the resultant mixture was introduced into the crystallization apparatus, thus obtaining 9,850 g of purified acrylic acid (g).

The composition of the resultant waste oil was as follows: acrylic acid 75.3 weight %, acetic acid 4.0 weight %, propionic acid 2.7 weight %, water 2.7 weight %, and others 15.3 weight %; and the composition of the resultant purified acrylic acid (g) was as follows: acrylic acid 99.97 weight %, acetic acid 0.01 weight %, propionic acid 0.01 weight %, water 0.01 weight %, and the total content of hydroquinone and benzoquinone was 1.10 ppm. Purified acrylic acid (g) was neutralized in the same way as of Example 1, thus obtaining purified sodium acrylate (h) as a 37 weight % aqueous solution.

Before the crude acrylic acid was purified by distillation, hydroquinone was added thereto such that the total content therein of hydroquinone and benzoquinone would be 500 ppm in Example 1, whereas 1,500 ppm in Comparative Example 1. As a result, therefore, the total content of hydroquinone and benzoquinone in purified acrylic acid (a) in Example 1 was 0.15 ppm, whereas that in purified acrylic acid (e) in Comparative Example 1 increased to 1.20 ppm.

Similarly, before the crude acrylic acid was purified by crystallization, hydroquinone was added thereto such that the total content therein of hydroquinone and benzoquinone would be 500 ppm in Example 2, whereas 1,500 ppm in Comparative Example 2. As a result, therefore, the total content of hydroquinone and benzoquinone in purified acrylic acid (c) in Example 2 was 0.10 ppm, whereas that in purified acrylic acid (g) in Comparative Example 2 increased to 1.10 ppm.

EXAMPLE 3

(Polymerization of Acrylic Acid Having a Content of 0.15 ppm in total of HQ and BQ)

A stainless twin-arm type kneader of 10 liters in capacity having a jacket and two sigma type vanes of 120 mm in rotation diameter was used as the reactor. This kneader further had a cover for sealing up the system. Then, 376.3 g of purified acrylic acid (a), 3,983 g of sodium acrylate (b) ((a) and (b) were both obtained in Example 1), 640.7 g of ion-exchange water, and 2.775 g of trimethylolpropane triacrylate (as the crosslinking agent) were put into the sigma type twin-arm kneader to prepare a reaction solution, and the internal atmosphere of the system was then replaced with nitrogen by blowing a nitrogen gas into the system. Next, while warm water of 30° C. was run through the jacket and while the reaction solution was stirred, sodium persulfate and L-ascorbic acid were added thereto as polymerization initiators, so that a polymerization reaction got started about 1 minute after. The polymerization reaction was carried out at 30~80° C., and the resultant hydrogel polymer was got out 60 minutes after the initiation of the polymerization. The resultant hydrogel polymer was spread on a wire net of 50 mesh and dried at 160° C. with hot air for 65 minutes. Then, the resultant dried product was pulverized with a vibration mill and further classified with a wire net of 20 mesh, thus obtaining water-absorbent resin (1).

The coloring with time of water-absorbent resin (1) was evaluated. The result is shown in Table 1.

EXAMPLE 4

(Polymerization of Acrylic Acid Having a Content of 0.10 ppm in Total of HQ and BQ)

Water-absorbent resin (2) was obtained in the same way as of Example 3 except that purified acrylic acid (c) and sodium acrylate (d) were used.

The coloring with time of water-absorbent resin (2) was evaluated. The result is shown in Table 1.

COMPARATIVE EXAMPLE 3

(Polymerization of Acrylic Acid Having a Content of 1.10 ppm in Total of HQ and BQ)

Water-absorbent resin (3) was obtained in the same way as of Example 3 except that purified acrylic acid (e) and sodium acrylate (f) were used.

The coloring with time of water-absorbent resin (3) was evaluated. The result is shown in Table 1.

COMPARATIVE EXAMPLE 4

(Polymerization of Acrylic Acid Having a Content of 1.20 ppm in Total of HQ and BQ)

Water-absorbent resin (4) was obtained in the same way as of Example 3 except that purified acrylic acid (g) and sodium acrylate (h) were used.

The coloring with time of water-absorbent resin (4) was evaluated. The result is shown in Table 1.

EXAMPLE 5

(Addition of Quinhydronation Inhibitor)

First, 95 weight parts of water-absorbent resin (3) was uniformly blended with 5 weight parts of N,N'-methylenebisacrylamide under dry conditions. Then, the coloring with time was evaluated. The result is shown in Table 1.

EXAMPLE 6

(Addition of Quinhydronation Inhibitor)

First, 99 weight parts of water-absorbent resin (3) was uniformly blended with 1 weight part of N,N'-methylenebisacrylamide under dry conditions. Then, the coloring with time was evaluated. The result is shown in Table 1.

EXAMPLE 7

(Addition of Quinhydronation Inhibitor)

First, 95 weight parts of water-absorbent resin (4) was uniformly blended with 5 weight parts of N,N'-methylenebisacrylamide under dry conditions. Then, the coloring with time was evaluated. The result is shown in Table 1.

EXAMPLE 8

(Addition of Quinhydronation Inhibitor)

First, 99 weight parts of water-absorbent resin (4) was uniformly blended with 1 weight part of N,N'-methylenebisacrylamide under dry conditions. Then, the coloring with time was evaluated. The result is shown in Table 1.

EXAMPLE 9

(Addition of HQ and Quinhydronation Inhibitor)

First, 95 weight parts of water-absorbent resin (2) was mixed with 5 weight parts of a 0.02 weight % aqueous hydroquinone solution, thus obtaining water-absorbent resin (5). Next, 99 weight parts of water-absorbent resin (5) was uniformly blended with 1 weight part of N,N'-methylenebisacrylamide under dry conditions. Then, the coloring with time was evaluated. The result is shown in Table 1.

EXAMPLE 10

(Addition of HQ and Quinhydronation Inhibitor)

First, 95 weight parts of water-absorbent resin (2) was mixed with 5 weight parts of a 0.2 weight % aqueous hydroquinone solution, thus obtaining water-absorbent resin (6). Next, 99 weight parts of water-absorbent resin (6) was uniformly blended with 1 weight part of N,N'-methylenebisacrylamide under dry conditions. Then, the coloring with time was evaluated. The result is shown in Table 1.

COMPARATIVE EXAMPLE 5

(Addition of HQ)

The coloring with time of water-absorbent resin (5) was evaluated. The result is shown in Table 1.

COMPARATIVE EXAMPLE 6

(Addition of HQ)

The coloring with time of water-absorbent resin (6) was evaluated. The result is shown in Table 1.

EXAMPLE 11

(Addition of Impurities)

First, 99 weight parts of water-absorbent resin (2) was mixed with 1 weight part of hydroquinone monomethyl ether, thus obtaining water-absorbent resin (7). Then, the coloring with time of water-absorbent resin (7) was evaluated. The result is shown in Table 1.

EXAMPLE 12

(Addition of Impurities)

First, 99 weight parts of water-absorbent resin (2) was mixed with 1 weight part of acrolein, thus obtaining water-absorbent resin (8). Then, the coloring with time of water-absorbent resin (8) was evaluated. The result is shown in Table 1.

EXAMPLE 13

(Addition of Impurities)

First, 99 weight parts of water-absorbent resin (2) was mixed with 1 weight part of benzaldehyde, thus obtaining water-absorbent resin (9). Then, the coloring with time of water-absorbent resin (9) was evaluated. The result is shown in Table 1.

EXAMPLE 14

(Addition of Impurities)

First, 99 weight parts of water-absorbent resin (2) was mixed with 1 weight part of acetic acid, thus obtaining water-absorbent resin (10). Then, the coloring with time of water-absorbent resin (10) was evaluated. The result is shown in Table 1.

EXAMPLE 15

(Addition of Impurities)

First, 99 weight parts of water-absorbent resin (2) was mixed with 1 weight part of propionic acid, thus obtaining water-absorbent resin (11). Then, the coloring with time of water-absorbent resin (11) was evaluated. The result is shown in Table 1.

EXAMPLE 16

(Addition of Impurities)

First, 99 weight parts of water-absorbent resin (2) was mixed with 1 weight part of furfural, thus obtaining water-absorbent resin (12). Then, the coloring with time of water-absorbent resin (12) was evaluated. The result is shown in Table 2.

COMPARATIVE EXAMPLE 7

(Polymerization of Acrylic Acid Having a Content of 1.10 ppm in Total of HQ and BQ)

A stainless twin-arm type kneader of 10 liters in capacity having a jacket and two sigma type vanes of 120 mm in rotation diameter was used as the reactor. This kneader further had a cover for sealing up the system. Then, 376.3 g of purified acrylic acid (e), 3,983 g of sodium acrylate (f) ((e) and (f) were both obtained in Comparative Example 2), 640.7 g of ion-exchange water, and 1.617 g of N,N'-methylenebisacrylamide (as the crosslinking agent) were put into the sigma type twin-arm kneader to prepare a reaction solution, and the internal atmosphere of the system was then replaced with nitrogen by blowing a nitrogen gas into the system. Next, while warm water of 30° C. was run through the jacket and while the reaction solution was stirred, sodium persulfate and L-ascorbic acid were added thereto as polymerization initiators, so that a polymerization reaction got started about 1 minute after. The polymerization reaction was carried out at 30–80° C., and the resultant hydrogel polymer was got out 60 minutes after the initiation of the polymerization. The resultant hydrogel polymer was spread on a wire net of 50 mesh and dried at 160° C. with hot air for 65 minutes. Then, the resultant dried product was pulverized with a vibration mill and further classified with a wire net of 20 mesh, thus obtaining water-absorbent resin (13).

The coloring with time of water-absorbent resin (13) was evaluated. The result is shown in Table 1.

COMPARATIVE EXAMPLE 8

(Polymerization of Acrylic Acid Having a Content of 1.10 ppm in Total of HQ and BQ)

Water-absorbent resin (14) was obtained in the same way as of Comparative Example 7 except that 16.17 g of N,N'-methylenebisacrylamide was used as the crosslinking agent.

The coloring with time of water-absorbent resin (14) was evaluated. The result is shown in Table 1.

EXAMPLES 17~19

(Addition of Impurities)

Transition metals (which are regarded in JP-A-05-086251 as a factor of the coloring) 2 ppm (relative to the water-absorbent resin) along with water 10%, that is, aqueous solutions of Fe (iron nitrate 1,000 ppm standard solution, available from Wako Pure Chemical Industries, Ltd.), Ni (nickel nitrate 1,000 ppm standard solution, available from Wako Pure Chemical Industries, Ltd.), and Mn (manganese chloride standard solution, available from Kishida Kagaku), were added to 100 g of water-absorbent resin (1) (as obtained in Example 3), and then they were dried at 100° C., thus obtaining water-absorbent resins (15)~(17). Then, the coloring with time of water-absorbent resins (15)~(17) was evaluated. The results are shown in Table 2.

EXAMPLES 20, 21

(Influence of Particle Size)

Water-absorbent resin (1), as obtained in Example 3, was classified with a JIS standard sieve to divide the resin into three portions with respective particle diameters of 850~600 μm (water-absorbent resin (18)), 600–300 μm, and 300~150 μm (water-absorbent resin (19)). Then, the coloring with time was evaluated for Example 20 (powder of 850~600 μm) and Example 21 (powder of 300~150 μm) subsequently to Example 1 (powder of 600~300 μm). The results are shown in Table 2.

COMPARATIVE EXAMPLE 9

(Tracing Test of JP-A-05-086251)

Water-absorbent resin (3), as obtained in Comparative Example 3, was mixed with 1-hydroxyethylidene-1,1-diphosphonic acid 0.5 weight % (coloring inhibitor as disclosed in JP-A-05-086251) as an aqueous solution (water 10%) and then dried, thus obtaining water-absorbent resin (20). Then, the coloring with time of water-absorbent resin (20) was evaluated. The result is shown in Table 2.

COMPARATIVE EXAMPLES 10, 11

(Additives)

Water-absorbent resin (3), as obtained in Comparative Example 3, was mixed with hydrogen peroxide 0.5 weight % or sodium hydrogensulfite 0.5 weight % (which were commercially available bleaching agents) as an aqueous solution (water 10 weight %) and then dried, thus obtaining water-absorbent resins (21), (22), of which the coloring with time was evaluated. The results are shown in Table 2. Incidentally, the arts of adding these additives to water-absorbent resins are disclosed in the following publications: EP 780424, U.S. Pat. No. 4,959,060, U.S. Pat. No. 4,972,019, U.S. Pat. No. 4,929,717, and U.S. Pat. No. 5,229,488.

COMPARATIVE EXAMPLES 12~14

(Additives)

In Comparative Example 9, water-absorbent resin (3) was mixed with polylysine (Comparative Example 12), polyvaline (Comparative Example 13), and polyglycine (Comparative Example 14) (all these polyamino acids have a molecular weight of about 5,000), 1 weight % each, as aqueous solutions (water 10 weight %) to trap transition metals, and then dried, thus obtaining water-absorbent resins (23)~(25), of which the coloring with time was evaluated. The results are shown in Table 2. Incidentally, the arts of adding these polyamino acids to water-absorbent resins are disclosed in EP 668080.

COMPARATIVE EXAMPLE 15

(Washing)

First, 100 g of water-absorbent resin (3), as obtained in Comparative Example 3, was stirred along with 100 cc of a 50 weight % aqueous ethanol solution for 30 minutes, and then filtrated, and dried at 50° C. Incidentally, the arts of washing water-absorbent resins are disclosed in the following publications: EP 780424, EP 837076, and U.S. Pat. No. 4,794,166.

EXAMPLE 22

(Production of Acid Water-absorbent Resin Powder (1))

Trimethylolpropane triacrylate (internal-crosslinking agent) was dissolved by 0.02 mol % into 5,500 g of an aqueous solution of sodium acrylate with a neutralization ratio of 55 mol % (concentration of monomer in this aqueous solution: 33 weight %) as prepared using acrylic acid with a content of 0.15 ppm in total of hydroquinone and benzoquinone as obtained in Example 1, and the resultant aqueous monomer solution (1) was degassed with a nitrogen gas for 30 minutes and then supplied into a reaction vessel as prepared by capping a stainless twin-arm type kneader of 10 liters in capacity having two sigma-type vanes and a jacket. While the temperature in the reaction system was kept at 20° C., the replacement of the atmosphere inside the reaction vessel with nitrogen was continued. Next, while the vanes were rotated, 0.12 g/mol (relative to monomer) of sodium persulfate and 0.005 g/mol of L-ascorbic acid (polymerization initiators) were added as an aqueous solution each. As a result, about 1 minute after, polymerization got started, and 11 minutes after, the reaction mixture reached the peak temperature of 91° C. Then, the aqueous solution polymerization was continued still under stirring, while the resultant hydrogel polymer was integrated into minute particles of about 5 mm~about 1 mm or less, and the stirring was continued. Then, 40 minutes later than the initiation of the polymerization, the resultant hydrogel polymer (1) was got out.

The minute particles of the resultant hydrogel polymer (1) were spread on a wire net of 300 $\mu$m (50 mesh) in mesh size and then dried at 150° C. with a hot air for 2 hours. The resultant dry product was pulverized with a roll mill and then classified with a screen of 850 $\mu$m in mesh size, thus obtaining acid water-absorbent resin powder (26) of the irregular pulverized shape. The properties of the resultant acid water-absorbent resin powder (26) are as follows: pH=5.4, water absorption capacity under no load=36.0 g/g, water-soluble content=20 weight %.

EXAMPLE 23

(Production of Acid Water-absorbent Resin Powder (2)):

The nitrogen replacement was carried out in the same way as of Example 22 except that the monomer as used for the aqueous solution polymerization was aqueous monomer solution (2) as prepared by dissolving trimethylolpropane triacrylate (internal-crosslinking agent) by 0.05 mol % into 5,022 g of an aqueous solution of sodium acrylate with a neutralization ratio of 40 mol % (monomer concentration: 30 weight %) as obtained using acrylic acid with a content of 0.15 ppm in total of hydroquinone and benzoquinone, and that the temperature of the nitrogen replacement was 42° C. Thereafter, the aqueous solution polymerization was carried out in the same way as of Example 22, so that the peak temperature was 91° C. The minute particles of the resultant hydrogel polymer (2) were spread on a wire net of 300 $\mu$m (50 mesh) in mesh size and then dried at 150° C. with a hot air for 2.5 hours. The resultant dry product was pulverized and classified in the same way as of Example 22, thus obtaining acid water-absorbent resin powder (27) of the irregular pulverized shape. The properties of the resultant acid water-absorbent resin powder (27) are as follows: pH=4.9, water absorption capacity under no load=31.5 g/g, water-soluble content=10 weight %.

EXAMPLE 24

(Production of Acid Water-absorbent Resin Powder (3))

The nitrogen replacement was carried out in the same way as of Example 22 except that the monomer as used for the aqueous solution polymerization was aqueous monomer solution (3) as prepared by dissolving trimethylolpropane triacrylate (internal-crosslinking agent) by 0.05 mol % into 5,295 g of an aqueous solution of sodium acrylate with a neutralization ratio of 50 mol % (monomer concentration: 37 weight %) as obtained using acrylic acid with a content of 0.15 ppm in total of hydroquinone and benzoquinone, and that the temperature of the nitrogen replacement was 27° C. Thereafter, the aqueous solution polymerization was carried out in the same way as of Example 22, so that the peak temperature was 95° C. The minute particles of the resultant hydrogel polymer (3) were dried, pulverized, and classified in the same way as of Example 23, thus obtaining acid water-absorbent resin powder (28) of the irregular pulverized shape. The properties of the resultant acid water-absorbent resin powder (28) are as follows: pH=5.2, water absorption capacity under no load=30.6 g/g, water-soluble content=5 weight %.

EXAMPLE 25

(Production of Acid Water-absorbent Resin Powder (4))

The nitrogen replacement was carried out in the same way as of Example 22 except that the monomer as used for the aqueous solution polymerization was aqueous monomer solution (4) as prepared by dissolving trimethylolpropane triacrylate (internal-crosslinking agent) by 0.05 mol % into 5,295 g of an aqueous solution of sodium acrylate with a neutralization ratio of 58 mol % (monomer concentration: 37 weight %) as obtained using acrylic acid with a content of 0.15 ppm in total of hydroquinone and benzoquinone, and that the temperature of the nitrogen replacement was 27° C. Thereafter, the aqueous solution polymerization was carried out in the same way as of Example 22, so that the peak temperature was 92° C. The minute particles of the resultant hydrogel polymer (4) were dried, pulverized, and classified in the same way as of Example 23, thus obtaining acid water-absorbent resin powder (29) of the irregular pulverized shape. The properties of the resultant acid water-absorbent resin powder (29) are as follows: pH=5.5, water absorption capacity under no load=37.0 g/g, water-soluble content=7.5 weight %.

EXAMPLE 26

(Production of Acid Water-absorbent Resin Powder (5))

Nitrogen replacement was carried out for an aqueous monomer solution, comprising 151 g (0.7 mol %) of N,N'-methylenebisacrylamide, 39,609 g of ion-exchange water, and a mixture of hydroquinone 0.05 ppm and 10,088 g of acrylic acid of 0.15 ppm in total content of hydroquinone and benzoquinone, while the temperature of the aqueous monomer solution was kept at 27° C. Next, 100.8 g of a 10 weight % aqueous hydrogen peroxide solution, 305.2 g of a 10 weight % aqueous 2,2'-azobis(amidinopropane) dihydrochloride (product name: V-50, available from Wako Pure Chemical Industries, Ltd.), and 252 g of a 1 weight % aqueous L-ascorbic acid solution were added thereto as polymerization initiators to carry out adiabatic polymerization for 2 hours. The resultant hydrogel polymer (5) was cut into the size of several mm with a meat chopper and then dried at 60° C. with a hot air and then further dried at 60° C. under decompression, and then dried, pulverized, and classified in the same way as of Example 23, thus obtaining acid water-absorbent resin powder (30) of the irregular pulverized shape. The properties of the resultant acid water-absorbent resin powder (30) are as follows: pH=3.0, water absorption capacity under no load=6 g/g (value in 24 hours), water-soluble content=2 weight %. In addition, as to the coloring degree (YI) of the acid water-absorbent resin powder (30), YI=3.0 just after production, YI=5.2 after test (after 1 week), and the change of the coloring degree, ΔYI, was 2.2.

EXAMPLE 27

(Production of Water-absorbent Resin Powder (6))

Neutral water-absorbent resin powder (31), displaying pH=6.1, of the irregular pulverized shape was obtained by polymerization, drying, and pulverization in the same way as of Example 22 except that the sodium acrylate was changed to sodium acrylate with a neutralization ratio of 75 mol % as obtained using acrylic acid with a content of 0.15 ppm in total of hydroquinone and benzoquinone.

EXAMPLE 28

(Surface-crosslinking (1) of Acid Water-absorbent Resin)

A crosslinking agent composition, comprising 1 weight part of 1,4-butanediol, 3 weight parts of water, and 0.5 weight part of isopropanol, was added to 100 weight parts of acid water-absorbent resin powder (26) (as obtained in Example 22), and the resultant mixture was heated at 180° C. for 22 minutes, thus obtaining water-absorbing agent (1).

The properties of water-absorbing agent (1) are as follows: pH=5.4, absorption capacity for a physiological salt solution under a load of 20 g/cm$^2$=30.4 g/g, water absorption capacity under no load=28.4 g/g, absorption capacity for a physiological salt solution under a load of 50 g/cm$^2$=23.1 g/g, absorption capacity for artificial urine under a load of 50 g/cm$^2$=28.4 g/g, average particle diameter=300 μm, and amount of residual monomer=250 ppm. The results are shown in Table 3.

EXAMPLE 29

(Surface-crosslinking of Neutral Water-absorbent Resin: Case of pH Exceeding 5.5)

As is shown in Table 3, the properties of water-absorbing agent (2), as obtained by surface-crosslinking neutral water-absorbent resin (31) (sodium polyacrylate crosslinked product of neutralization ratio=75 mol % and pH=6.1 as obtained in Example 27) in the same way as of Example 28, are pH=6.1 and almost the same as those of water-absorbing agent (1), for example, with regard to absorption capacity for a physiological salt solution under a load of 20 g/cm$^2$. In addition, the average particle diameter was 300 μm, and the amount of residual monomer was 400 ppm. The reaction duration of the surface-crosslinking was about 40 minutes, and thus about twice as long a period as that in Example 28 was needed. The results are shown in Table 3.

EXAMPLE 30

(Surface-crosslinking (2) of Acid Water-absorbent Resin)

A crosslinking agent, comprising 0.1 weight part of ethylene glycol diglycidyl ether, 1 weight part of propylene glycol, 3 weight parts of water, and 3 weight parts of isopropanol, was added to 100 weight parts of acid water-absorbent resin powder (27) (as obtained in Example 23), and the resultant mixture was heated at 150° C. for 20 minutes, thus obtaining water-absorbing agent (3) having an average particle diameter of 300 μm. The results are shown in Table 3.

EXAMPLE 31

(Surface-crosslinking (3) of Acid Water-absorbent Resin)

A crosslinking agent, comprising 0.1 weight part of ethylene glycol diglycidyl ether, 1 weight part of propylene glycol, 3 weight parts of water, and 3 weight parts of isopropanol, was added to 100 weight parts of acid water-absorbent resin powder (28) (as obtained in Example 24) in the same way as of Example 30, and the resultant mixture was heated at 150° C. for 20 minutes, thus obtaining water-absorbing agent (4) having an average particle diameter of 300 μm. The results are shown in Table 3.

EXAMPLE 32

(Surface-crosslinking (4) of Acid Water-absorbent Resin)

A crosslinking agent, comprising 0.1 weight part of ethylene glycol diglycidyl ether, 1 weight part of propylene glycol, 3 weight parts of water, and 3 weight parts of isopropanol, was added to 100 weight parts of acid water-absorbent resin powder (29) (as obtained in Example 25) in the same way as of Example 30, and the resultant mixture was heated at 150° C. for 20 minutes, thus obtaining water-absorbing agent (5) having an average particle diameter of 300 μm. The results are shown in Table 3.

COMPARATIVE EXAMPLE 16

(Comparative Surface-crosslinking)

Neutral water-absorbent resin powder (32), displaying pH=6.1, of the irregular pulverized shape was obtained by polymerization, drying, and pulverization in the same way as of Example 22 except that the sodium acrylate was changed to sodium acrylate with a neutralization ratio of 75 mol % as obtained using acrylic acid with a content of 0.50 ppm in total of hydroquinone and benzoquinone as prepared by further adding hydroquinone 0.35 ppm. Next, the surface neighborhood of the resultant water-absorbent resin powder (32) was crosslinked to obtain comparative water-absorbing agent (1). The results are shown in Table 3.

COMPARATIVE EXAMPLE 17

(Commercially Available Water-absorbent Resins)

The properties such as coloring and absorption capacity under a load were compared with regard to water-absorbent resins (the bulky ones were used for measurement of the absorption capacity under a load) as separated from commercially available diapers. The results are shown in Table 4.

COMPARATIVE EXAMPLE 18

(Coloring Evaluation Similar to JP-A-05-086251)

The coloring evaluation method, similar to examples of preferred embodiments as set forth in JP-A-05-086251, was carried out in the below-mentioned way for water-absorbent resin (4) with a content of 1.10 ppm in total of hydroquinone and benzoquinone as obtained in Comparative Example 3. Water-absorbent resin (4) was placed into a polyethylene bag of 60 μm in thickness and closed by heat-sealing, and then left at 70° C. under 65% RH for 1 week. After 1 week, the closed water-absorbent resin was opened, and the coloring degree (YI) was evaluated in the same way as above. The results are shown in Table 5. Incidentally, the measurement apparatus and conditions of the coloring are different from the conditions as set forth in JP-A-05-086251, so the present Comparative Example 18 is a comparison between the closed system (JP-A-05-086251) and the open system (the present invention).

EXAMPLES 33~35

(Influence of Water Content)

Water-absorbent resin (1), as obtained in Example 3, was further dried to obtain water-absorbent resin (33) with a water content of 0.2% or below. Next, 5 g, 11, g, and 25 g of water was sprayed to and thereby absorbed by this water-absorbent resin (33), and then left, thus obtaining a water content of about 5% (water-absorbent resin (34)), about 10% (water-absorbent resin (35)), and about 20% (water-absorbent resin (36)) respectively. As to the resultant water-absorbent resin (34)~(36), the coloring test similar to JP-A-05-086251 was carried out in the same way as of Comparative Example 18. The results are shown in Table 5.

EXAMPLE 36

(Disposable Diaper)

An absorbent structure was produced in the following way using water-absorbent resin (1) as obtained in Example 3, and then a disposable diaper was produced as a sanitary material.

First, 50 weight parts of water-absorbent resin (1) and 50 weight parts of wood-pulverized pulp (hydrophilic fiber) were mixed together in a dry manner with a mixer.

Next, the resultant mixture was shaped into a web of the size of 120 mm×400 mm by pneumatically molding the mixture on a wire screen of 400 mesh (mesh size: 38 μm) (according to JIS) with a batch type pneumatic device. In addition, this web was pressed for 5 seconds under a pressure of 2 kg/cm$^2$, thus obtaining an absorbent structure, which had a resin concentration of 50 weight % and a basis weight of about 0.047 g/cm$^2$. Incidentally, the water-absorbent resin and the wood-pulverized pulp can easily and uniformly be mixed.

Next, a back sheet, the above absorbent structure, and a top sheet were attached to each other in this order with double coated tapes, wherein the back sheet was made of liquid-impermeable polypropylene and cut into the predetermined shape, and the top sheet was made of liquid-permeable polypropylene and cut into almost the same shape as that of the back sheet. Then, a so-called leg gather and a so-called waist gather were made at respective predetermined positions of the resultant attachment product. Furthermore, so-called tape fasteners were then provided at predetermined positions of the attachment product, thus obtaining a disposable diaper.

This disposable diaper was left at 70° C. under 65% RH atmosphere for 1 week in a thermo-hydrostat (model No. PL-2G made by Tabai Especk Co., Ltd.) to evaluate the coloring with time. As a result, the appearance did not discolor when compared with what it had been before the test.

EXAMPLE 37

(Disposable Diaper)

A disposable diaper was produced using the water-absorbent resin (as obtained in Example 6) in the same way as of Example 36. Then, the coloring with time of this disposable diaper was evaluated in the same way as of Example 36. As a result, the appearance did not discolor when compared with what it had been before the test.

COMPARATIVE EXAMPLE 19

(Comparative Disposable Diaper)

A disposable diaper was produced using water-absorbent resin (3) (as obtained in Comparative Example 3) in the same way as of Example 36. Then, the coloring with time of this disposable diaper was evaluated in the same way as of Example 36. As a result, as to the disposable diaper after the test, the existence of dark brown spots were seen with the eye through the top sheet when compared with what it had been before the test.

EXAMPLE 38

(Sanitary Napkin)

Sanitary napkin (1) was obtained by incorporating water-absorbing agent (2) (as obtained in Example 22) into pulp of commercially available sanitary napkin free from water-absorbent resin. The coloring of the resultant sanitary napkin (1) of α=0.5 was evaluated out in the same way as of Example 23. In the evaluation of the coloring with time, the appearance did not discolor when compared with what it had been before the test.

COMPARATIVE EXAMPLE 20

(Comparative Sanitary Napkin)

Comparative sanitary napkin (1) was obtained in the same way as of Example 38 except that water-absorbing agent (2) was replaced with comparative water-absorbing agent (1). Then, the coloring evaluation was carried out in the same way as above. As a result, the existence of dark brown spots on the surface of the napkin were seen with the eye.

EXAMPLE 39

First, 195.23 g of acrylic acid of 0.20 ppm in total content of hydroquinone and benzoquinone was prepared by adding hydroquinone 0.05 ppm to acrylic acid of 0.15 ppm in total content of hydroquinone and benzoquinone, and then neutralized to obtain lithium acrylate, of which 1,749.99 g of a 30 weight % aqueous solution was uniformly mixed with 3.91 g (0.085 mol % relative to monomer) of polyethylene glycol diacrylate (crosslinking agent) and 1,012.17 g of ion-exchange water to prepare a partially neutralized aqueous lithium acrylate solution, which was placed into a cylindrical vessel and degassed with a nitrogen gas. Next, while the partially neutralized aqueous lithium acrylate solution was kept at 14° C., 9.44 g of a 10 weight % aqueous 2,2'-azobis(amidinopropane) dihydrochloride (trade name: V-50, available from Wako Pure Chemical Industries, Ltd.), 9.44 g of a 10 weight % aqueous sodium persulfate solution, 14.16 g of a 10 weight % aqueous hydrogen peroxide solution, and 6.61 g of a 1 weight % aqueous L-ascorbic acid solution were added and mixed as polymerization initiators, so that polymerization got started about 1 minute after. Then, the static adiabatic polymerization was continued for 1.5 hours. The resultant hydrogel polymer was got out of the reaction vessel and placed into a kneader with a jacket of 70° C. The blade was rotated for 15 minutes to cut the hydrogel into the size of about 1~about 5 mm, and the hydrogel was then dried with a hot-air dryer of 160° C. for 1 hour. The resultant dry product was pulverized with laboratory pulverizer and then allowed to pass a JIS standard sieve to separate a portion of 850~150 μm in particle diameter. The properties of the resultant water-absorbent resin powder (37) are as follows: coloring degree YI=6.9 just after separation, water absorption capacity under no load 49.6 g/g, water-soluble content=13.0 weight %.

TABLE 1

| | Absorption capacity (g/g) | Coloring degree (YI value) | | | HQ content *1 (ppm) | MBAA content | MBAA/ HQ |
|---|---|---|---|---|---|---|---|
| | | Before test | After test | Change of coloring degree | | | |
| Example 3 | 46 | 3.6 | 6.8 | 3.2 | 0.15 | — | — |
| Example 4 | 46 | 3.5 | 6.6 | 3.1 | 0.10 | — | — |
| Comparative Example 3 | 45 | 3.4 | 45.1 | 41.7 | 1.20 | — | — |
| Comparative Example 4 | 46 | 3.3 | 47.6 | 44.3 | 1.10 | — | — |
| Example 5 | 45 | 3.4 | 6.9 | 3.5 | 1.20 | 5.0% *2 | 43860 |
| Example 6 | 46 | 3.4 | 6.8 | 3.4 | 1.20 | 1.0% *2 | 8418 |
| Example 7 | 45 | 3.3 | 7.1 | 3.8 | 1.10 | 5.0% *2 | 47847 |
| Example 8 | 46 | 3.4 | 6.9 | 3.5 | 1.10 | 1.0% *2 | 9183 |
| Example 9 | 44 | 3.4 | 7.0 | 3.6 | 10.1 | 1.0% *2 | 1000 |
| Example 10 | 45 | 3.6 | 7.1 | 3.5 | 100.1 | 1.0% *2 | 101 |
| Comparative Example 5 | 44 | 3.5 | 44.8 | 41.3 | 10.1 | — | — |
| Comparative Example 6 | 44 | 3.9 | 46.8 | 42.9 | 100.1 | — | — |
| Example 11 | 44 | 3.5 | 6.6 | 3.1 | 0.10 | — | — |
| Example 12 | 44 | 3.4 | 6.9 | 3.5 | 0.10 | — | — |
| Example 13 | 44 | 3.5 | 6.6 | 3.1 | 0.10 | — | — |
| Example 14 | 43 | 3.4 | 6.9 | 3.5 | 0.10 | — | — |
| Example 15 | 43 | 3.5 | 6.6 | 3.1 | 0.10 | — | — |
| Comparative Example 7 | 42 | 13.8 | 45.3 | 31.5 | 1.20 | N.D. *3 | — |
| Comparative Example 8 | 25 | 14.5 | 45.3 | 30.8 | 1.20 | N.D. *3 | 1.7 |

*1 Total content of hydroquinone and benzoquinone in water-absorbent resin or in acrylic acid (AA)
*2 N,N'-methylenebisacrylamide content (= MBAA/(water-absorbent resin + MBAA))
*3 Amount of N,N'-methylenebisacrylamide remaining in water-absorbent resin was measured (N.D. = Non-Detectable).

TABLE 2

| | Absorption capacity g/g | Coloring degree (YI value) Before test | Coloring degree (YI value) After test | Change of coloring degree | HQ content *1 (ppm) |
|---|---|---|---|---|---|
| Example 16 | 43 | 3.5 | 6.8 | 3.4 | 0.10 |
| Example 17 | 46 | 8.7 | 13.3 | 5.6 | 0.10 |
| Example 18 | 46 | 7.1 | 15.1 | 7.9 | 0.10 |
| Example 19 | 46 | 6.8 | 13.4 | 7.6 | 0.10 |
| Example 20 | 46 | 4.0 | 7.8 | 3.8 | 0.10 |
| Example 21 | 46 | 3.2 | 6.0 | 2.8 | 0.10 |
| Comparative Example 9 | 45 | 4.6 | 28.3 | 23.7 | 1.10 |
| Comparative Example 10 | 45 | 3.0 | 51.5 | 48.5 | 1.10 |
| Comparative Example 11 | 45 | 3.2 | 34.4 | 31.2 | 1.10 |
| Comparative Example 12 | 45 | 3.2 | 45.2 | 42.0 | 1.20 |
| Comparative Example 13 | 45 | 3.1 | 43.9 | 40.8 | 1.20 |
| Comparative Example 14 | 45 | 3.7 | 43.7 | 40.0 | 1.20 |
| Comparative Example 15 | 45 | 3.4 | 44.4 | 41.0 | 1.20 |

*1: Total content of hydroquinone and benzoquinone in water-absorbent resin or in acrylic acid (AA)

TABLE 3

| | pH | Water absorption capacity (g/g) under no load | Absorption capacity (g/g) under load Physiological salt solution (20 g/cm²) | Absorption capacity (g/g) under load Physiological salt solution (50 g/cm²) | Absorption capacity (g/g) under load Artifical urine (50 g/cm²) | Blocking ratio (wt %) | Residual monomer (ppm) | Hygroscopicity (wt %) | Coloring degree (YI value) Before test | Coloring degree (YI value) After test | Change of coloring degree |
|---|---|---|---|---|---|---|---|---|---|---|---|
| Water-absorbing agent (1) | 5.3 | 28.4 | 30.4 | 23.1 | 28.4 | 10~15 | 250 | 1.7 | 4.9 | 8.9 | 4.0 |
| Water-absorbing agent (2) | 6.1 | 28.3 | 30.1 | 22.1 | 28.1 | 100~90 | 400 | 4.8 | 4.0 | 9.0 | 5.0 |
| Water-absorbing agent (3) | 4.9 | 26.2 | 26.1 | 22.3 | 27.9 | 10 or below | 180 | 0.7 | 6.1 | 8.8 | 2.7 |
| Water-absorbing agent (4) | 5.2 | 27.4 | 27.2 | 23.2 | 30.4 | 10 or below | 180 | 1.5 | 4.8 | 8.9 | 4.1 |
| Water-absorbing agent (5) | 5.5 | 29.0 | 29.9 | 25.0 | 32.5 | 20~15 | 180 | 2.2 | 4.7 | 8.7 | 4.0 |
| Comparative water-absorbing agent (1) | 6.1 | 28.2 | 30.0 | 22.1 | 27.7 | 100~90 | 410 | 4.8 | 3.4 | 45.2 | 41.8 |
| Water-absorbent resin powder (31) | 6.1 | — | 10 or below | 10 or below | 10 or below | — | 400 | — | 3.6 | 6.8 | 3.2 |

TABLE 4

| Purchase country | Month/year of purchase | Maker | Diaper name (size) | Shape of water-absorbent resin | Water absorption capacity (g/g) under no load | Absorption capacity (g/g) for physiological salt solution under load (50 g/cm²) | Coloring degree (YI value) Before test | Coloring degree (YI value) After test | Change of coloring degree |
|---|---|---|---|---|---|---|---|---|---|
| United Kingdom | April 1998 | Procter & Gamble | Pampers Premium (Max) | Irregular | 31 | 20 | 27.4 | 49.1 | 21.7 |
| | June 1998 | Kimbery-Clark Corporation | Huggies Boys (Maxi) | Irregular | 28 | 11 | 22.9 | 38.8 | 15.9 |
| USA | May 1998 | Procter & Gamble | Pampers Premium (21 lbs) | Irregular | 30 | 15 | 12.6 | 42.4 | 29.8 |

TABLE 4-continued

| Purchase country | Month/year of purchase | Maker | Diaper name (size) | Shape of water-absorbent resin | Water absorption capacity (g/g) under no load | Absorption capacity (g/g) for physiological salt solution under load (50 (g/cm$^2$) | Coloring degree (YI value) Before test | After test | Change of coloring degree |
|---|---|---|---|---|---|---|---|---|---|
| | May 1998 | Kimbery-Clark Corporation | Huggies Supreme (22–37 lbs) | Irregular | 30 | 18 | 9.1 | 41.4 | 32.3 |
| Japan | October 1998 | Kao Co., Ltd. | Super Merries (L) | Reversed phase | 48 | 7 | 19.1 | 21.1 | 2.0 |
| | August 1998 | UNI-CHARM K.K. | Moony Power Slim (L) | Irregular | 37 | 8 | 11.6 | 36.8 | 25.2 |
| | March 1998 | UNI-CHARM K.K. | Mummy Poco (L) | Irregular | 35 | 13 | 13.4 | 38.2 | 24.8 |
| | May 1998 | Nepia Co., Ltd. | Doremi Sara-Sara Fit (L) | Irregular | 31 | 19 | 13.3 | 36.1 | 22.8 |
| | June 1998 | Daio Seishi Co., Ltd. | Elleair Friend Super Fit (L) | Irregular | 37 | 21 | 9.0 | 31.7 | 22.7 |

TABLE 5

| | Absorption capacity g/g | Coloring degree (YI value) Before test | After test | Change of coloring degree | HQ content *1 (ppm) |
|---|---|---|---|---|---|
| Comparative Example 18 | 46 | 3.4 | 17.0 | 16.6 | 1.10 |
| Example 33 | 46 | 3.6 | 4.2 | 0.6 | 0.15 |
| Example 34 | 44 | 3.7 | 4.5 | 0.8 | 0.15 |
| Example 35 | 39 | 3.7 | 6.8 | 3.1 | 0.15 |

*1: Total content of hydroquinone and benzoquinone in water-absorbent resin

In Examples 3 and 4, combinations of acrylic acid and its salt having a content of 0.15 ppm and 0.10 ppm respectively in total of hydroquinone and benzoquinone are used as starting materials, so the extent of the change of the coloring degree is very little. In comparison with this, in Comparative Examples 3 and 4, combinations of acrylic acid and its salt having a content of 1.20 ppm and 1.10 ppm respectively in total of hydroquinone and benzoquinone are used as starting materials, so the extent of the change of the coloring degree is very great.

In Examples 5 to 8, N,N'-methylenebisacrylamide is added as the quinhydronation inhibitor to the water-absorbent resins of Comparative Examples 3 and 4 having a great content in total of hydroquinone and benzoquinone, so the extent of the change of the coloring degree is very little.

In Comparative Examples 5 and 6, hydroquinone is added to the water-absorbent resin of Example 4, so the extent of the change of the coloring degree is very great. In Examples 9 and 10, N,N'-methylenebisacrylamide is added as the quinhydronation inhibitor to the water-absorbent resins of Comparative Examples 5 and 6, so the extent of the change of the coloring degree is very little.

In Examples 11 to 16, impurities other than hydroquinone are added to the water-absorbent resin of Example 4, but these impurities do not influence the coloring, so the extent of the change of the coloring degree is as very little as that in Example 4.

In Comparative Examples 7 and 8, N,N'-methylenebisacrylamide is used as the internal-crosslinking agent, but bound into the resin as the crosslinking agent, so there is no effect as the quinhydronation inhibitor, thus resulting in no effect of preventing the change of the coloring.

In Comparative Example 9, an organic phosphoric acid compound (1-hydroxyethylidene-1,1-diphosphonic acid which is a coloring inhibitor, as disclosed in JP-A-05-086251, for water-absorbent resins) was used. Indeed this compound may display a coloring prevention effect, but is inferior to the present invention method in which the total content of hydroquinone and benzoquinone is reduced to 0.20 ppm or below. In addition, the above organic phosphoric acid compound gives a YI value of around 12 after 1 week under the evaluation conditions according to JP-A-05-086251, but gives a YI value higher than 20 after 1 week under the test conditions according to the present invention. From this result, it would be understood that the present invention evaluation is stricter than the prior art one.

In Comparative Examples 10 and 11, hydrogen peroxide and sodium hydrogensulfite were used respectively as commercially available bleaching agents. From their results, it would be understood that the sodium hydrogensulfite displays a little effect, but is much inferior to the present invention.

In Examples 17~19, transition metals, which are regarded in JP-A-05-086251 as a factor of the coloring of the water-absorbent resin, were added in a large amount of 2 ppm. From their results, it would be understood that these transition metals, however, hardly contribute to the coloring when compared with the total content of hydroquinone and benzoquinone of 0.20 ppm. Incidentally, JP-A-05-086251 discloses heavy metals of 0.1~0.01 ppm as impurities of water-absorbent resins.

In Examples 20, 21, and 3, the influence of the particle size of the water-absorbent resin was examined. From their results, it would be understood that the larger the particle size is, the greater the coloring is.

In Comparative Examples 9~14, various additives, including those which are disclosed in JP-A-05-086251, were added. From their results, it would be understood that these additives, however, display little or no effect when compared with the present invention.

In Examples 22~27, the influence of pH of the water-absorbent resin was examined. From their results, it would be understood that the lower the pH value is, the less the coloring is.

In Examples 29~32 and Comparative Example 16, the influence of the crosslinking of the surface neighborhood of the water-absorbent resin was examined. Water-absorbing agents (1)~(5) according to the present invention display less coloring and higher absorption capacity under a load than the commercially available product as set forth in Comparative Example 15. Furthermore, it would also be understood that the surface-crosslinking promotes the coloring. In addition, the depression of pH lessens residual monomers in water-absorbing agents or the hygroscopic amount (weight %). Particularly, as to water-absorbing agents (1)~(4), the blocking resistance under high humidity conditions is greatly improved to 15 weight % or below.

Comparative Example 17 is a commercially available water-absorbent resin, which becomes greatly colored and displays lower absorption capacity under a load when compared with the present invention.

Comparative Example 18 is a coloring evaluation method in the closed system similar to JP-A-05-086251. From results thereof, it would be understood that the conditions in this method are looser than the coloring evaluation (Comparative Example 3) in the present invention.

In Examples 33~35, the influence of the water content was examined by the coloring evaluation method in the closed system similar to JP-A-05-086251. From their results, it would be understood that the higher the water content is (particularly, around 20% exceeding 10%), the easier the coloring is.

From the results of Examples 36~38 and Comparative Examples 19~20, it would be understood that the water-absorbent resin according to the present invention displays little coloring even in absorbent articles.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A crosslinked water-absorbent resin which is internally-crosslinked, which is obtained by aqueous solution polymerization or reverse-phase suspension polymerization, which has a water-soluble content of 25 weight % or below, which has an absorption capacity of 20 g/g or more for a physiological salt solution under a load of 50 g/cm$^2$, over a period of 60 minutes, wherein the physiological salt solution is 0.9 wt % aqueous sodium chloride solution and which is obtained by a process comprising the steps of:
    a) producing an acrylic acid, wherein hydroquinone is used in the step of producing the acrylic acid in an amount greater than 0.20 ppm "based on acrylic acid";
    b) reducing a total amount of hydroquinone and benzoquinone in the acrylic acid or its salt to at most 0.20 ppm "based on acrylic acid";
    c) providing a monomer component, wherein a major portion of the monomer component is one or both of the acrylic acid or its salt; and
    d) polymerizing the monomer component to obtain the crosslinked water-absorbent resin.

2. A crosslinked water-absorbent resin according to claim 1, wherein polymerization of the monomer component is aqueous solution polymerization.

3. A crosslinked water-absorbent resin according to claim 1, obtained by a process further including the step of heat-drying at 100~300° C. within 3 hours after the step of polymerizing the monomer component.

4. A crosslinked water-absorbent resin according to claim 1, comprising particles of an irregular pulverized shape, of which 50 weight % or more have a particle diameter of 300 μm or more.

5. A crosslinked water-absorbent resin according to claim 1, which has a water content of at most 2 weight %.

6. A crosslinked water-absorbent resin according to claim 1, which is a partially neutralized resin.

7. A crosslinked water-absorbent resin having a water-soluble content of 25 weight % or below, comprising a major proportion of an acrylic polymer which is obtained by a process including the step of polymerizing a monomer component including a major proportion of either one or both of acrylic acid and its salt, wherein the crosslinked water-absorbent resin has an absorption capacity of 20 g/g or more for a physiological salt solution under a load of 50 g/cm$^2$ over a period of 60 minutes, wherein the physiological salt solution is 0.9 wt % aqueous sodium chloride solution, and wherein the coloring degree (YI) is at most 20 after the crosslinked water-absorbent resin is left exposed to the atmosphere at 70° C. and 65% RH for 1 week.

8. A crosslinked water-absorbent resin according to claim 7, which displays a change of the coloring degree (YI) by at most 4.

9. A crosslinked water-absorbent resin according to claim 7, wherein the acrylic polymer is a polymer as obtained by a process including the step of aqueous solution polymerization.

10. A crosslinked water-absorbent resin according to claim 7, comprising particles of the irregular pulverized shape, of which 50 weight % or more have a particle diameter of 300 μm or more.

11. A crosslinked water-absorbent resin according to claim 1, which displays a pH of 5.5 or less in a physiological salt solution that is a 0.9 wt % aqueous sodium chloride solution.

12. A crosslinked water-absorbent resin according to claim 1, of which 50 weight % or more have a particle diameter of 300 μm or more.

13. A crosslinked water-absorbent resin according to claim 7, which displays a pH of 5.5 or less in a physiological salt solution that is a 0.9 wt % aqueous sodium chloride solution.

14. A crosslinked water-absorbent resin according to claim 7, of which 50 weight % or more have a particle diameter of 300 μm or more.

15. A crosslinked water-absorbent resin according to claim 1, wherein the amount of hydroquinone used in the producing process for acrylic acid is not less than 10 ppm "based on acrylic acid".

16. A crosslinked water-absorbent resin having a water-soluble content of 25 weight % or below and further having an absorption capacity of 20 g/g or more for a physiological salt solution under a load of 50 g/cm$^2$ over a period of 60 minutes wherein the physiological salt solution is a 0.9 wt % aqueous sodium chloride solution, wherein the crosslinked water-absorbent resin is obtained by a process including the step of polymerizing a monomer component including a major proportion of either one or both of acrylic acid and its salt which have a content of at most 0.20 ppm in total of hydroquinone and benzoquinone "based on acrylic acid".

17. A crosslinked water-absorbent resin which has an absorption capacity of 20 g/g or more for a physiological salt solution under a load of 50 g/cm$^2$ over a period of 60 minutes wherein the physiological salt solution is a 0.9 wt % aqueous sodium chloride solution, which has a water-soluble content of 25 weight % or below and which is obtained by a process comprising the steps of:
    a) producing an acrylic acid, wherein hydroquinone is used in the step of producing the acrylic acid in an amount greater than 0.20 ppm "based on acrylic acid";
    b) reducing a total amount of hydroquinone and benzoquinone in the acrylic acid or its salt to at most 0.20 ppm "based on acrylic acid";
    c) providing a monomer component, wherein a major portion of the monomer component is one or both of the acrylic acid or its salt; and
    d) polymerizing the monomer component to obtain the cross-linked water-absorbent resin.

* * * * *